US011311189B2

United States Patent
Hirose et al.

(10) Patent No.: US 11,311,189 B2
(45) Date of Patent: Apr. 26, 2022

(54) OPHTHALMIC IMAGING APPARATUS, CONTROLLING METHOD THEREOF, OPHTHALMIC IMAGING METHOD, AND RECORDING MEDIUM

(71) Applicant: TOPCON CORPORATION, Tokyo (JP)

(72) Inventors: Ryoichi Hirose, Itabashi-ku (JP); Toshihiro Mino, Warabi (JP); Tatsuo Yamaguchi, Warabi (JP)

(73) Assignee: TOPCON CORPORATION, Tokyo (JP)

( * ) Notice: Subject to any disclaimer, the term of this patent is extended or adjusted under 35 U.S.C. 154(b) by 336 days.

(21) Appl. No.: 16/543,625

(22) Filed: Aug. 19, 2019

(65) Prior Publication Data

US 2020/0093364 A1     Mar. 26, 2020

(30) Foreign Application Priority Data

Sep. 26, 2018   (JP) .............................. JP2018-180763

(51) Int. Cl.
*A61B 3/10* (2006.01)
*A61B 3/14* (2006.01)
(Continued)

(52) U.S. Cl.
CPC ................ *A61B 3/102* (2013.01); *A61B 3/14* (2013.01); *A61B 3/12* (2013.01); *A61B 3/135* (2013.01); *G06T 2207/30041* (2013.01)

(58) Field of Classification Search
CPC .. A61B 3/102; A61B 3/14; A61B 3/12; A61B 3/135; G06T 2207/30041
(Continued)

(56) References Cited

U.S. PATENT DOCUMENTS

| 2005/0195360 A1* | 9/2005 | Akita ..................... A61B 3/135 |
| | | 351/212 |
| 2013/0301008 A1 | 11/2013 | Srivastava et al. |

(Continued)

FOREIGN PATENT DOCUMENTS

| JP | 2009-183332 A | 8/2009 |
| JP | 2015-515894 A | 6/2015 |

(Continued)

OTHER PUBLICATIONS

Jaeken et al., "Optical Quality of Emmetropic and Myopic Eyes in the Periphery Measured with High-Angular Resolution", Investigative Ophthalmology & Visual Science, vol. 53, No. 7, Jun. 2012, pp. 3405-3413.

(Continued)

*Primary Examiner* — Mohammed A Hasan
(74) *Attorney, Agent, or Firm* — Xsensus LLP

(57) ABSTRACT

An ophthalmic imaging apparatus of an exemplary aspect includes a data acquisition device, image constructing circuitry, and composing circuitry. The data acquisition device is configured to sequentially apply optical coherence tomography (OCT) scans to a plurality of regions different from each other of a fundus of a subject's eye in order and under a condition according to a fundus shape, to acquire a plurality of pieces of data corresponding to the plurality of regions. The image constructing circuitry is configured to construct an image from each of the plurality of pieces of data. The composing circuitry is configured to construct a composite image of a plurality of images constructed from the plurality of pieces of data by the image constructing circuitry.

11 Claims, 10 Drawing Sheets

(51) Int. Cl.
*A61B 3/12* (2006.01)
*A61B 3/135* (2006.01)

(58) Field of Classification Search
USPC .......................................................... 351/206
See application file for complete search history.

(56) References Cited

U.S. PATENT DOCUMENTS

| | | |
|---|---|---|
| 2016/0038023 A1 | 2/2016 | Endo et al. |
| 2016/0317029 A1 | 11/2016 | Srivastava et al. |
| 2017/0189228 A1* | 7/2017 | Yang ...................... A61B 3/102 |
| 2017/0236282 A1* | 8/2017 | Abramoff .............. A61B 3/102 |
| | | 382/131 |
| 2018/0168445 A1 | 6/2018 | Horn |
| 2019/0059720 A1 | 2/2019 | Kubota |
| 2019/0365220 A1 | 12/2019 | Frisken et al. |

FOREIGN PATENT DOCUMENTS

| | | |
|---|---|---|
| JP | 2017-153543 A | 9/2017 |
| WO | 2018/136993 A1 | 8/2018 |

OTHER PUBLICATIONS

Extended European Search Report dated Feb. 4, 2020, issued in corresponding European Patent Application No. 19195482.5.

\* cited by examiner

OPHTHALMIC IMAGING APPARATUS, CONTROLLING METHOD THEREOF, OPHTHALMIC IMAGING METHOD, AND RECORDING MEDIUM

CROSS-REFERENCE TO RELATED APPLICATION

This application is based upon and claims the benefit of priority from Japanese Patent Application No. 2018-180763, filed Sep. 26, 2018; the entire contents of which are incorporated herein by reference.

FIELD

Embodiments described herein relate generally to an ophthalmic imaging apparatus, controlling method thereof, an ophthalmic imaging method, and a recording medium.

BACKGROUND

Importance of diagnostic imaging and image analysis is increasing in ophthalmic examinations. In particular, the application of optical coherence tomography (OCT) to ophthalmology is encouraging this trend. The OCT enables three dimensional imaging as well as three dimensional structural analysis and functional analysis of a subject's eye, and serves an effective role for acquiring distributions of various measurement values, for example.

In recent years, the expansion of OCT scan area, in other words the enlargement of the angle of view of OCT (OCT scan angle), has been advanced in order to enable wide area observation from the central part to the peripheral part of the eye fundus. Widening the angle of view requires the enlargement of the depth range according to the bowl shape of the eye fundus, in addition to the enlargement of the scan length (the length of B-scan). However, there is a restriction in widening the angle of view, for example, from the requirement that OCT scans have to be performed through the eye pupil.

Therefore, a technique is employed in which a plurality of regions different from one another are scanned to construct a plurality of images, and the constructed images are composed to obtain a wide area image (see Japanese Unexamined Patent Application Publication No. 2009-183332, for example). This method is referred to as montage (photomontage), collage (photocollage), panoramic composition, and the like.

On the other hand, considering the bowl shape of the fundus and the aberration distribution of the eye, imaging for montage (referred to as montage imaging) requires the adjustments of various kinds of conditions such as the focal position, OCT optical path length and polarization conditions each time the imaging region is changed. Note that the ocular aberration distribution is described, for example, in Bart Jaeken, Pablo Artal, "Optical Quality of Emmetropic and Myopic Eyes in the Periphery Measured with High-Angular Resolution", Investigative Ophthalmology & Visual Science, June 2012, Vol. 53, No. 7, pp. 3405-3413, and it is known that the defocus amounts are largely different between the central parts and the peripheral parts of eye funduses.

Here, while the optical scanner that produces OCT scanning can operate at extremely high speed, the operations of focus adjustment and optical path length adjustment take a longer time compared to the operation of the optical scanner as they involve movement of optical elements caused by the actuator. Therefore, the focus adjustment and the optical path length adjustment may become bottlenecks in speeding up montage imaging, that is, they may become bottle necks in shortening the time taken for the montage imaging, despite they are necessary for the improvement in image quality.

SUMMARY

An object of exemplary aspects is to achieve both shortening of time required for montage imaging and improvement of image quality.

An ophthalmic imaging apparatus according to the first aspect of some exemplary embodiments includes a data acquisition device, image constructing circuitry, and composing circuitry. The data acquisition device is configured to sequentially apply optical coherence tomography (OCT) scans to a plurality of regions different from each other of a fundus of a subject's eye in order and under a condition both according to a fundus shape, to acquire a plurality of pieces of data corresponding to the plurality of regions. The image constructing circuitry is configured to construct an image from each of the plurality of pieces of data. The composing circuitry is configured to construct a composite image of a plurality of images constructed from the plurality of pieces of data by the image constructing circuitry.

The second aspect of some exemplary embodiments is the ophthalmic imaging apparatus of the first aspect, further including order setting circuitry that sets the order according to the fundus shape.

The third aspect of some exemplary embodiments is the ophthalmic imaging apparatus of the second aspect, wherein the data acquisition device applies a preparatory OCT scan to the fundus prior to applying the OCT scans to the plurality of regions, the image constructing circuitry constructs a preparatory image from data acquired through the preparatory OCT scan, and the order setting circuitry analyzes the preparatory image to generate shape information on the fundus and sets the order based on the shape information.

The fourth aspect of some exemplary embodiments is the ophthalmic imaging apparatus of the third aspect, wherein the order setting circuitry determines a depth position distribution of the fundus as the shape information and sets the order based on the depth position distribution.

The fifth aspect of some exemplary embodiments is the ophthalmic imaging apparatus of the second aspect, wherein the order setting circuitry sets the order based on standard shape information indicating a standard fundus shape generated in advance.

The sixth aspect of some exemplary embodiments is the ophthalmic imaging apparatus of the first aspect, further including region setting circuitry that sets the plurality of regions.

The seventh aspect of some exemplary embodiments is the ophthalmic imaging apparatus of the sixth aspect, wherein the data acquisition device applies a preparatory OCT scan to the fundus prior to applying the OCT scans to the plurality of regions, the image constructing circuitry constructs a preparatory image from data acquired through the preparatory OCT scan, and the region setting circuitry analyzes the preparatory image to generate shape information on the fundus and sets the plurality of regions based on the shape information.

The eighth aspect of some exemplary embodiments is the ophthalmic imaging apparatus of the sixth aspect, wherein the region setting circuitry sets the plurality of regions based on standard shape information indicating a standard fundus shape generated in advance.

The ninth aspect of some exemplary embodiments is the ophthalmic imaging apparatus of the first aspect, further including condition setting circuitry that sets the condition according to the fundus shape.

The tenth aspect of some exemplary embodiments is the ophthalmic imaging apparatus of the ninth aspect, wherein for each of the plurality of regions, the data acquisition device applies a preparatory OCT scan to a concerned region (any one of the plurality of regions), the image constructing circuitry constructs a preparatory image of the concerned region from data acquired from the concerned region through the preparatory OCT scan, and the condition setting circuitry analyzes the preparatory image of the concerned region to determine a depth position of the fundus in the concerned region and sets a condition applied to an OCT scan of the concerned region based on the depth position for the concerned region.

The eleventh aspect of some exemplary embodiments is the ophthalmic imaging apparatus of the ninth aspect, wherein the data acquisition device applies a preparatory OCT scan to the fundus prior to applying the OCT scans to the plurality of regions, the image constructing circuitry constructs a preparatory image from data acquired through the preparatory OCT scan, and the condition setting circuitry analyzes the preparatory image to generate shape information on the fundus and sets conditions respectively applied to the OCT scans for the plurality of regions based on the shape information.

The twelfth aspect of some exemplary embodiments is the ophthalmic imaging apparatus of the eleventh aspect, wherein the condition setting circuitry determines a depth position distribution of the fundus as the shape information and sets the conditions respectively applied to the OCT scans for the plurality of regions based on the depth position distribution.

The thirteenth aspect of some exemplary embodiments is the ophthalmic imaging apparatus of ninth aspect, wherein the condition setting circuitry sets the conditions respectively applied to the OCT scans for the plurality of regions based on standard shape information indicating a standard fundus shape generated in advance.

The fourteenth aspect of some exemplary embodiments is the ophthalmic imaging apparatus of any of the first to thirteenth aspects, wherein the data acquisition device includes a measurement arm that forms a path of measurement light projected onto the fundus for the OCT scans and a reference arm that forms a path of reference light superposed on the measurement light, and the condition includes an arm length condition that indicates at least one of a length of the measurement arm and a length of the reference arm. In addition, the ophthalmic imaging apparatus further includes an arm length changing device and first controlling circuitry. The arm length changing device changes at least one of the length of the measurement arm and the length of the reference arm. The first controlling circuitry controls the arm length changing device based on the arm length condition.

The fifteenth aspect of some exemplary embodiments is the ophthalmic imaging apparatus of any of the first to fourteenth aspects, wherein the condition includes a focus condition that indicates a focus state of a measurement arm that forms a path of measurement light projected onto the fundus for the OCT scans. In addition, the ophthalmic imaging apparatus further includes a focus state changing device and second controlling circuitry. The focus state changing device changes the focus state of the measurement arm. The second controlling circuitry controls the focus state changing device based on the focus condition.

The sixteenth aspect of some exemplary embodiments is a method of controlling an ophthalmic imaging apparatus that includes a data acquisition device configured to acquire data by applying optical coherence tomography (OCT) scan to a fundus of a subject and a processor configured to process the data acquired by the data acquisition device. The method includes the following steps: controlling the data acquisition device to sequentially apply OCT scans to a plurality of regions different from each other of the fundus in order and under a condition both according to a fundus shape, to acquire a plurality of pieces of data corresponding to the plurality of regions; controlling the processor to construct an image from each of the plurality of pieces of data; and controlling the processor to construct a composite image of a plurality of images constructed from the plurality of pieces of data.

The seventeenth aspect of some exemplary embodiments is a method of acquiring images of eyes. The ophthalmic imaging method includes the following steps: sequentially applying OCT scans to a plurality of regions different from each other of a fundus of a subject's eye in order and under a condition both according to a fundus shape, to acquire a plurality of pieces of data corresponding to the plurality of regions; constructing an image from each of the plurality of pieces of data; and constructing a composite image of a plurality of images constructed from the plurality of pieces of data.

The eighteenth aspect of some exemplary embodiments is a program that causes a computer to execute the method of the sixteenth aspect.

The nineteenth aspect of some exemplary embodiments is a program that causes an ophthalmic imaging apparatus to execute the method of the seventeenth aspect.

The twentieth aspect of some exemplary embodiments is a computer-readable non-transitory recording medium storing the program of the eighteenth aspect.

The twenty first aspect of some exemplary embodiments is a computer-readable non-transitory recording medium storing the program of the nineteenth aspect.

According to some exemplary embodiments, shortening of the time required for montage imaging and improvement of image quality both can be achieved.

DETAILED DESCRIPTION

Figure 1:
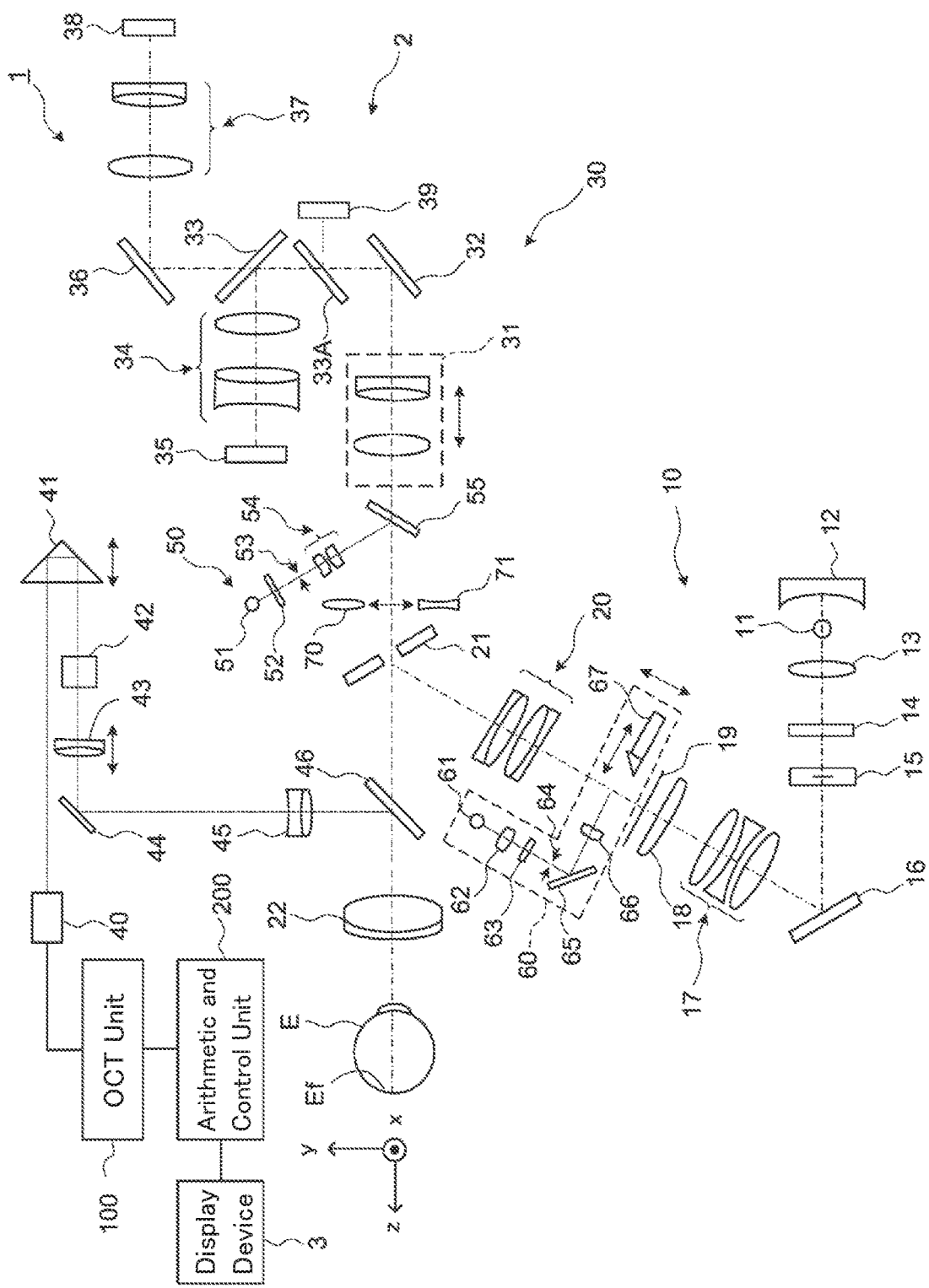
FIG. 1 is a schematic diagram illustrating an example of the configuration of an ophthalmic imaging apparatus according to an exemplary embodiment.

Ophthalmic imaging apparatuses according to some exemplary embodiments, methods of controlling ophthalmic imaging apparatuses according to some exemplary embodiments, ophthalmic imaging methods according to some exemplary embodiments, programs according to some exemplary embodiments, and recording media according to some exemplary embodiments will be described in detail with referring to the drawings. The disclosures of the documents cited in the present specification and/or any other known techniques can be incorporated into the embodiments. In addition, "image data" and an "image" based thereon are not distinguished from one another unless otherwise mentioned. Further, a "site" of the subject's eye and an "image" thereof are not distinguished from one another unless otherwise mentioned.

Ophthalmic imaging apparatuses according to some exemplary embodiments can perform imaging of the funduses of living eyes using Fourier domain OCT (e.g., swept source OCT). The type of OCT applicable to embodiments is not limited to swept source OCT, and spectral domain OCT or time domain OCT may be employed, for example.

Some exemplary embodiments may be capable of processing images acquired by modalities other than OCT. For example, some exemplary embodiments may be capable of processing images acquired using any of a fundus camera, a scanning laser ophthalmoscope (SL0), a slit lamp microscope, and an ophthalmic surgical microscope. An ophthalmic imaging apparatus according to some exemplary embodiments may include any of a fundus camera, an SL0, a slit lamp microscope, and an ophthalmic surgical microscope.

The images of the subject's eye that can be processed by some exemplary embodiments may include an image obtained by analyzing an image acquired by a modality of any kind. Examples of such an analyzed image include the followings: a pseudo-colored image (e.g., a segmented pseudo-color image); an image consisting only of part of the original image (e.g., a segment image); an image representing the thickness distribution of a tissue obtained by analyzing an OCT image (e.g., a layer thickness map or a layer thickness graph); an image representing the shape of a tissue (e.g., a curvature map); and an image representing the distribution of lesions (e.g., a lesion map).

<Configurations>

The ophthalmic imaging apparatus 1 of an exemplary embodiment shown in FIG. 1 includes the fundus camera unit 2, the OCT unit 100 and the arithmetic and control unit 200. The fundus camera unit 2 is provided with optical systems and mechanisms for acquiring front images of a subject's eye. The OCT unit 100 includes part of optical systems and part of mechanisms for performing OCT. Another part of the optical systems and another part of mechanisms for performing OCT is provided in the fundus camera unit 2. The arithmetic and control unit 200 includes one or more processors that perform various calculations, operations and controls. In addition to them, the ophthalmic apparatus 1 may also include arbitrary kinds of elements such as a member for supporting the face of the subject (e.g., a chin rest and/or a forehead rest), and/or arbitrary kinds of units such as a lens unit for switching the sites to which OCT is applied. An example of such a lens unit is an attachment for anterior eye segment OCT.

In the present specification, the term "processor" is used to mean, for example, a circuit (circuitry) such as a central processing unit (CPU), a graphics processing unit (GPU), an application specific integrated circuit (ASIC), a programmable logic device (for example, a simple programmable logic device (SPLD), a complex programmable logic device (CPLD), or a field programmable gate array (FPGA)), or the like. The processor realizes the functions according to the embodiment, for example, by reading out and executing a program stored in a storage circuit or a storage device.

<Fundus Camera Unit 2>

The fundus camera unit 2 is provided with optical systems for photographing the fundus Ef of the subject's eye E. Images of the fundus Ef (referred to as fundus images, fundus photographs, or the like) obtained by the fundus camera unit 2 are front images such as observation images and photographed images. An observation image is obtained, for example, by capturing a moving image using near-infrared light. The observation image is used in operations such as alignment, focusing, and tracking. A photographed image is, for example, a still image obtained by using visible or infrared flash light.

The fundus camera unit 2 includes the illumination optical system 10 and the photographing optical system 30. The illumination optical system 10 projects illumination light onto the subject's eye E. The photographing optical system 30 detects the return light of the illumination light from the subject's eye E. The measurement light incident from the OCT unit 100 is directed to the subject's eye E through the optical path in the fundus camera unit 2. In addition, the return light of the measurement light from the subject's eye E is directed to the OCT unit 100 through the same optical path.

The light output from the observation light source 11 of the illumination optical system 10 (referred to as observation illumination light) is reflected by the concave mirror 12, passes through the condenser lens 13, and becomes near-infrared light after passing through the visible cut filter 14. Further, the observation illumination light is once converged at a location near the photographing light source 15, reflected by the mirror 16, and passes through the relay lens system 17, the relay lens 18, the diaphragm 19, and the relay lens system 20. Then, the observation illumination light is reflected on the peripheral part (i.e., the surrounding area of the aperture part) of the aperture mirror 21, penetrates the dichroic mirror 46, and refracted by the objective lens 22, thereby illuminating the subject's eye E (the fundus Ef). The return light of the observation illumination light from the subject's eye E is refracted by the objective lens 22, penetrates the dichroic mirror 46, passes through the aperture part formed in the center area of the aperture mirror 21, passes through the dichroic mirror 55, travels through the photography focusing lens 31, and is reflected by the mirror 32. Further, the return light passes through the half mirror 33A, is reflected by the dichroic mirror 33, and forms an image on the light receiving surface of the image sensor 35 by the imaging lens 34. The image sensor 35 detects the return light at a predetermined frame rate (capture rate). Note that the focus (i.e., the focal position) of the photographing optical system 30 is adjusted to coincide with the fundus Ef or the anterior eye segment.

The light output from the photographing light source 15 (referred to as photographing illumination light) passes through the same route as that of the observation illumination light and is projected onto the fundus Ef. The return light of the photographing illumination light from the subject's eye E passes through the same route as that of the return light of the observation illumination light, is guided to the dichroic mirror 33, passes through the dichroic mirror 33, is reflected by the mirror 36, and forms an image on the light receiving surface of the image sensor 38 by the imaging lens 37.

The liquid crystal display (LCD) 39 displays a fixation target (i.e., a fixation target image). Part of the light beam output from the LCD 39 is reflected by the half mirror 33A, reflected by the mirror 32, travels through the photography focusing lens 31 and the dichroic mirror 55, and passes through the aperture part of the aperture mirror 21. The light beam having passed through the aperture part of the aperture mirror 21 penetrates the dichroic mirror 46, and is refracted by the objective lens 22, thereby being projected onto the fundus Ef.

By changing the display position of the fixation target image on the screen of the LCD 39, the fixation position of the subject's eye E by the fixation target can be changed. Examples of the fixation position includes the followings: a fixation position for acquiring an image centered on the macula; a fixation position for acquiring an image centered on the optic nerve head; a fixation position for acquiring an image centered on the position that is located between the macula and the optic nerve head; and a fixation position for acquiring an image of a site far away from the macula (i.e., a periphery of the fundus). A user interface such as a graphical user interface (GUI) for designating at least one of such typical fixation positions can be provided. Further, a user interface such as a GUI for manually changing the fixation position (i.e., the display position of the fixation target) can be provided.

The configuration for presenting the fixation target, which is capable of changing the fixation position, to the subject's eye E is not limited to display devices such as an LCD. For example, a fixation matrix can be adopted in place of a display device. The fixation matrix includes a plurality of light emitting parts (e.g., light emitting diodes) that are disposed in a matrix-like arrangement (in a matrix array). In this case, the fixation position of the subject's eye E by the fixation target can be changed by lighting one (or more) of the plurality of light emitting parts in a selective manner. As another example, the fixation target that is capable of changing the fixation position can be generated by employing one or more movable light emitting parts.

The alignment optical system 50 generates an alignment indicator used for the alignment of the optical system with respect to the subject's eye E. The alignment light output from the light emitting diode (LED) 51 travels through the diaphragm 52, the diaphragm 53, and the relay lens 54, is reflected by the dichroic mirror 55, passes through the aperture part of the aperture mirror 21, penetrates the dichroic mirror 46, and is projected onto the subject's eye E via the objective lens 22. The return light of the alignment light from the subject's eye E (the cornea reflection light, etc.) passes through the same route as that of the return light of the observation illumination light and is guided to the image sensor 35. Based on the received image (referred to as the alignment indicator image), manual alignment and/or automatic alignment can be performed.

As in a conventional case, the alignment indicator image of the present example includes two bright spot images whose positions change according to alignment states. When the relative position between the subject's eye E and the optical system changes in the xy direction, the two bright spot images are shifted in the xy direction in an integrated manner. When the relative position between the subject's eye E and the optical system changes in the z direction, the relative position (i.e., the distance) between the two bright spot images changes. When the distance between the subject's eye E and the optical system in the z direction matches a predetermined working distance, the two bright spot images overlap with each other. When the position of the subject's eye E matches the position of the optical system in the xy direction, the two bright spot images are presented within or near a given alignment target. When the distance between the subject's eye E and the optical system in the z direction matches the working distance, and the position of the subject's eye E matches the position of the optical system in the xy direction, the two bright spot images overlap with each other and are presented within the alignment target.

In the automatic alignment, the data processing circuitry 230 detects the positions of the two bright spot images, and the main controlling circuitry 211 controls the movement mechanism 150 (described later) on the basis of the positional relationship between the two bright spot images and the alignment target. In the manual alignment, the main controlling circuitry 211 displays the two bright spot images together with the observation image of the subject's eye E on the display device 241, and the user operates the movement mechanism 150 using the operation device 242 while referring to the two bright spot images displayed.

The focus optical system 60 generates a split indicator used for the focus adjustment with respect to subject's eye E. In conjunction with the movement of the photography focusing lens 31 along the optical path of the photographing optical system 30 (referred to as the photographing optical path), the focus optical system 60 is moved along the optical path of the illumination optical system 10 (referred to as the illumination optical path). The reflection rod 67 is inserted into and removed from the illumination optical path. Before performing focus adjustment, the reflective surface of the reflection rod 67 is arranged in the slanted state in the illumination optical path. The focus light output from the LED 61 passes through the relay lens 62, is split into two light beams by the split indicator plate 63, passes through the two-hole diaphragm 64. Then, the focus light is reflected by the mirror 65, is converged on the reflective surface of the reflection rod 67 by the condenser lens 66, and is reflected by the reflective surface. Further, the focus light travels through the relay lens 20, is reflected by the aperture mirror 21, and penetrates the dichroic mirror 46, thereby being projected onto the subject's eye E via the objective lens 22. The return light of the focus light from the subject's eye E (e.g., the fundus reflection light) passes through the same route as the return light of the alignment light and is guided to the image sensor 35. Based on the image (referred to as the split indicator image), manual focusing and/or automatic focusing can be performed.

The diopter correction lenses 70 and 71 can be selectively inserted into the photographing optical path between the aperture mirror 21 and the dichroic mirror 55. The diopter correction lens 70 is a positive lens (convex lens) for correcting high hyperopia. The diopter correction lens 71 is a negative lens (concave lens) for correcting high myopia.

The dichroic mirror 46 couples the optical path for fundus photography and the optical path for OCT (measurement arm). The dichroic mirror 46 reflects the light of wavelength bands used for OCT and transmits the light for fundus photography. Listed from the OCT unit 100 side, the collimator lens unit 40, the retroreflector 41, the dispersion compensation member 42, the OCT focusing lens 43, the optical scanner 44, and the relay lens 45 are arranged in the measurement arm.

The retroreflector 41 is movable in the directions indicated by the arrows in FIG. 1 (i.e., the incident and the emitting directions of the measurement light LS). Thereby, the length of the measurement arm is changed. The change in the measurement arm length can be utilized for correcting the optical path length according to the axial length and the fundus shape, and for adjusting the interference condition, for example.

Together with the dispersion compensation member 113 (described later) arranged in the reference arm, the dispersion compensation member 42 acts to equalize the dispersion characteristics of the measurement light LS and the dispersion characteristics of the reference light LR with each other.

The OCT focusing lens 43 is movable along the directions indicated by the arrows in FIG. 1 (i.e., along the optical axis of the measurement arm) in order to perform the focus adjustment of the measurement arm. Thereby, the focus state (e.g., the focal position or the focal length) of the measurement arm is changed. The ophthalmic imaging apparatus 1 may be capable of controlling the movement of the photography focusing lens 31, the movement of the focus optical system 60, and the movement of the OCT focusing lens 43 in an interlocking manner.

The optical scanner 44 is placed at a position substantially optically conjugate with the pupil of the subject's eye E. The optical scanner 44 deflects the measurement light LS guided through the measurement arm. An example of the optical scanner 44 is a galvano scanner that allows two dimensional scanning. The galvano scanner includes a galvano mirror for scanning in the x direction and a galvano mirror for scanning in the y direction. In this case, typically, one of the two galvano mirrors is placed at a position optically conjugate with the pupil of the subject's eye E, or the pupil conjugate position is placed between the two galvano mirrors. As a result, an OCT scan can be applied to the posterior eye segment with a scanning pivot that is placed at a position in the pupil of the subject's eye E or near the pupil, and therefore a wide area of the fundus Ef can be scanned.

<OCT Unit 100>

Figure 2:
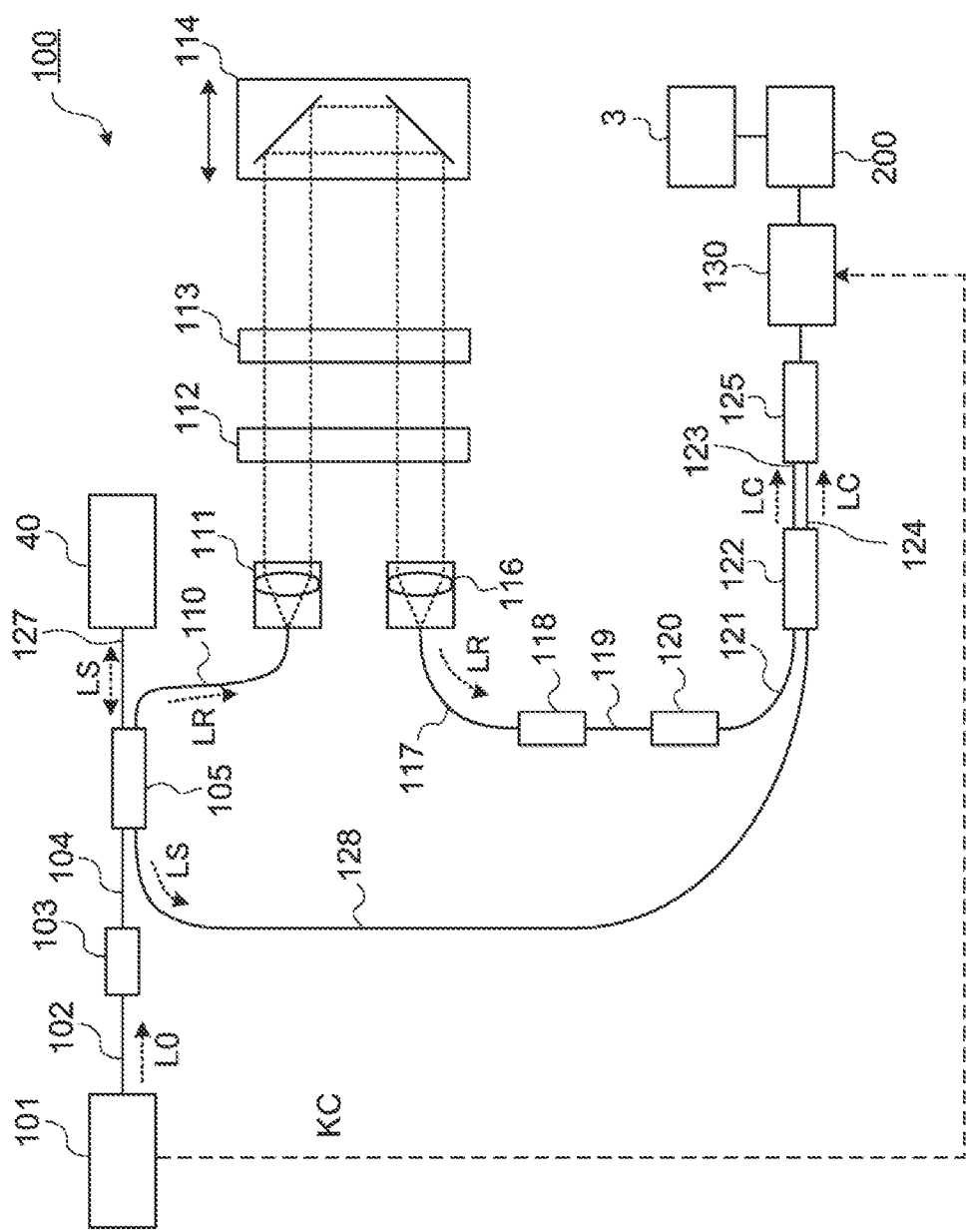
FIG. 2 is a schematic diagram illustrating an example of the configuration of the ophthalmic imaging apparatus according to the exemplary embodiment.

As illustrated in FIG. 2, the OCT unit 100 is provided with the optical system and mechanisms for applying swept source OCT. The optical system includes an interference optical system. The interference optical system is configured to split the light emitted from a wavelength tunable light source (also referred to as a wavelength swept light source) into measurement light and reference light, superpose the return light of the measurement light returned from the subject's eye E with the reference light having traveled through the reference optical path to generate interference light, and detect the interference light. The result of the detection (i.e., a detection signal) obtained by the interference optical system is a signal (i.e., interference signal) representing a spectrum of the interference light. The detection signal is sent to the arithmetic and control unit 200 (specifically, the image constructing circuitry 220).

The light source unit 101 includes, for example, a near infrared tunable laser configured to vary the wavelengths of emitted light at high speed. The light L0 output from the light source unit 101 is guided to the polarization controller 103 through the optical fiber 102, and the polarization state of the light L0 is regulated. Further, the light L0 is guided to the fiber coupler 105 through the optical fiber 104 and is split into the measurement light LS and the reference light LR. The optical path of the measurement light LS is referred to as a measurement arm, a sample arm, or the like, and the optical path of the reference light LR is referred to as a reference arm or the like.

The reference light LR is guided through the optical fiber 110 to the collimator 111, is converted into a parallel light beam, travels through the optical path length correction member 112 and the dispersion compensation member 113, and is guided to the retroreflector 114. The optical path length correction member 112 is an optical element for matching the optical path length of the reference light LR and the optical path length of the measurement light LS with each other. Together with the dispersion compensation member 42 arranged in the measurement arm, the dispersion compensation member 113 acts to equalize the dispersion characteristics of the reference light LR and the dispersion characteristics of the measurement light LS with each other. The retroreflector 114 is movable along the optical path of the reference light LR incident on the retroreflector 114. With this, the length of the reference arm is changed. The change in the reference arm length can be utilized, for example, for the correction of the optical path length according to the axial length and the fundus shape, and for the regulation of the interference condition.

After passing through the retroreflector 114, the reference light LR travels through the dispersion compensation member 113 and the optical path length correction member 112, is converted from a parallel light beam to a convergent light beam by the collimator 116, and is incident on the optical fiber 117. The reference light LR having entered the optical fiber 117 is guided to the polarization controller 118, and the polarization state of the reference light LR is regulated. The polarization controller 118 is an optical member for adjusting the interference condition, and is used, for example, to optimize the interference intensity between the measurement light LS and the reference light LR. The reference light LR having passed through the polarization controller 118 is guided to the attenuator 120 through the optical fiber 119, and the light amount of the reference light LR is regulated. Subsequently, the reference light LR is guided to the fiber coupler 122 through the optical fiber 121.

Meanwhile, the measurement light LS generated by the fiber coupler 105 is guided to the collimator lens unit 40 through the optical fiber 127 and is converted to a parallel light beam. After emitted from the collimator lens unit 40, the measurement light LS passes through the retroreflector 41, the dispersion compensation member 42, the OCT focusing lens 43, the optical scanner 44, and the relay lens 45, and then reaches the dichroic mirror 46. The measurement light LS is reflected by the dichroic mirror 46, is refracted by the objective lens 22, and is projected onto the subject's eye E. The measurement light LS is reflected and scattered at various depth positions of the subject's eye E. The return light of the measurement light LS returned from the subject's eye E travels along the same route as the outward way in the opposite direction, is directed to the fiber coupler 105, and then reaches the fiber coupler 122 via the optical fiber 128.

The fiber coupler 122 superposes the measurement light LS incident through the optical fiber 128 with the reference light LR incident through the optical fiber 121, to generate interference light. The fiber coupler 122 splits the generated interference light at a predetermined splitting ratio (e.g., the ratio is 1 to 1) to generate a pair of the interference light LC. The pair of the interference light LC is guided to the detector 125 respectively through the optical fibers 123 and 124.

The detector 125 includes, for example, a balanced photo diode. The balanced photodiode includes a pair of photodetectors for respectively detecting the pair of the interference light LC. The balanced photodiode outputs the difference between the pair of detection results obtained by the pair of photodetectors. The detector 125 sends the output (i.e., detection signal) to the data acquisition system (DAQ) 130.

The clock KC is supplied from the light source unit 101 to the data acquisition system 130. The clock KC is generated in the light source unit 101 in synchronization with the output timings of the respective wavelengths varied within a predetermined wavelength range by the wavelength tunable type light source. For example, the light source unit 101 splits the light L0 of each output wavelength to generate two pieces of split light, applies an optical delay to one of the two pieces of split light, superposes the two pieces of split light with each other, detects the superposed light, and generates the clock KC based on the detection result of the superposed light. The data acquisition system 130 uses the clock KC to perform the sampling of the detection signal input from the detector 125. The data acquisition system 130 sends the result of the sampling of the detection signal to the arithmetic and control unit 200.

The present example configuration is provided with both an element for changing the measurement arm length (e.g., the retroreflector 41) and an element for changing the reference arm length (e.g., the retroreflector 114 or a reference mirror); however, only one of these two elements may be provided in some other embodiments. An element for changing the difference between the measurement arm length and the reference arm length (i.e., an element for changing the optical path length difference) is not limited to the aforesaid elements, and may be any type of element (e.g., any type of an optical member, any type of a mechanism).

As described above, swept source OCT is a technique of constructing an image by splitting light emitted from a wavelength tunable light source into measurement light and reference light, superposing the return light of the measurement light returned from the object with the reference light to generate interference light, detecting the interference light by a light detector, and applying Fourier transform and other processes to the detected data acquired according to the wavelength sweeping and the measurement light scanning.

On the other hand, spectral domain OCT is a technique of constructing an image by splitting light emitted from a low coherence light source (i.e., a broadband light source) into measurement light and reference light, superposing the return light of the measurement light returned from the object with the reference light to generate interference light, detecting the spectral distribution of the interference light using a spectroscope (i.e. a spectrometer), and applying Fourier transform and other processes to the spectral distribution detected.

In short, swept source OCT is an OCT technique of acquiring a spectral distribution by time division, and spectral domain OCT is an OCT technique of acquiring a spectral distribution by space division.

<Control System and Processing System>

Figure 3:
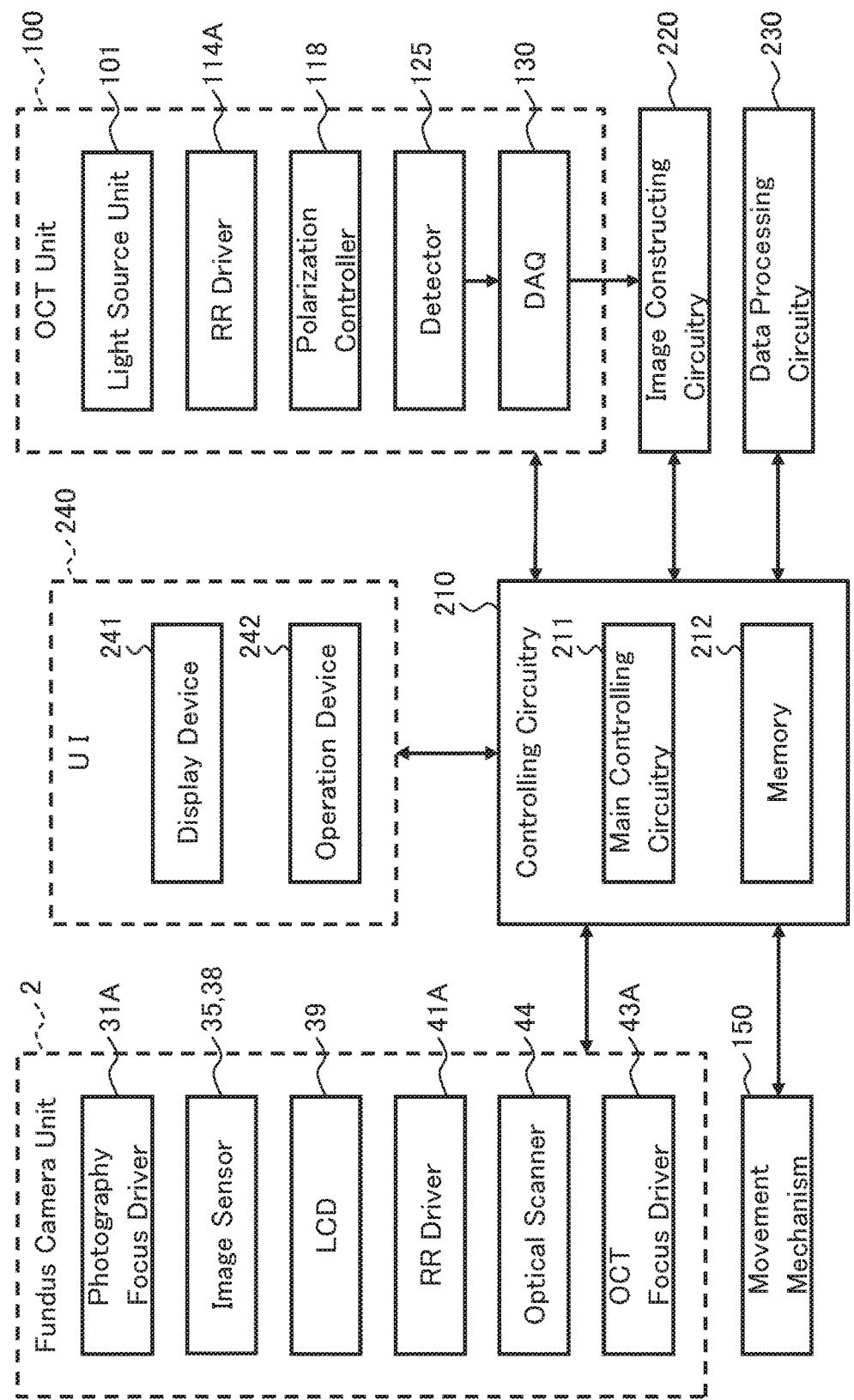
FIG. 3 is a schematic diagram illustrating an example of the configuration of the ophthalmic imaging apparatus according to the exemplary embodiment.
Figure 4:
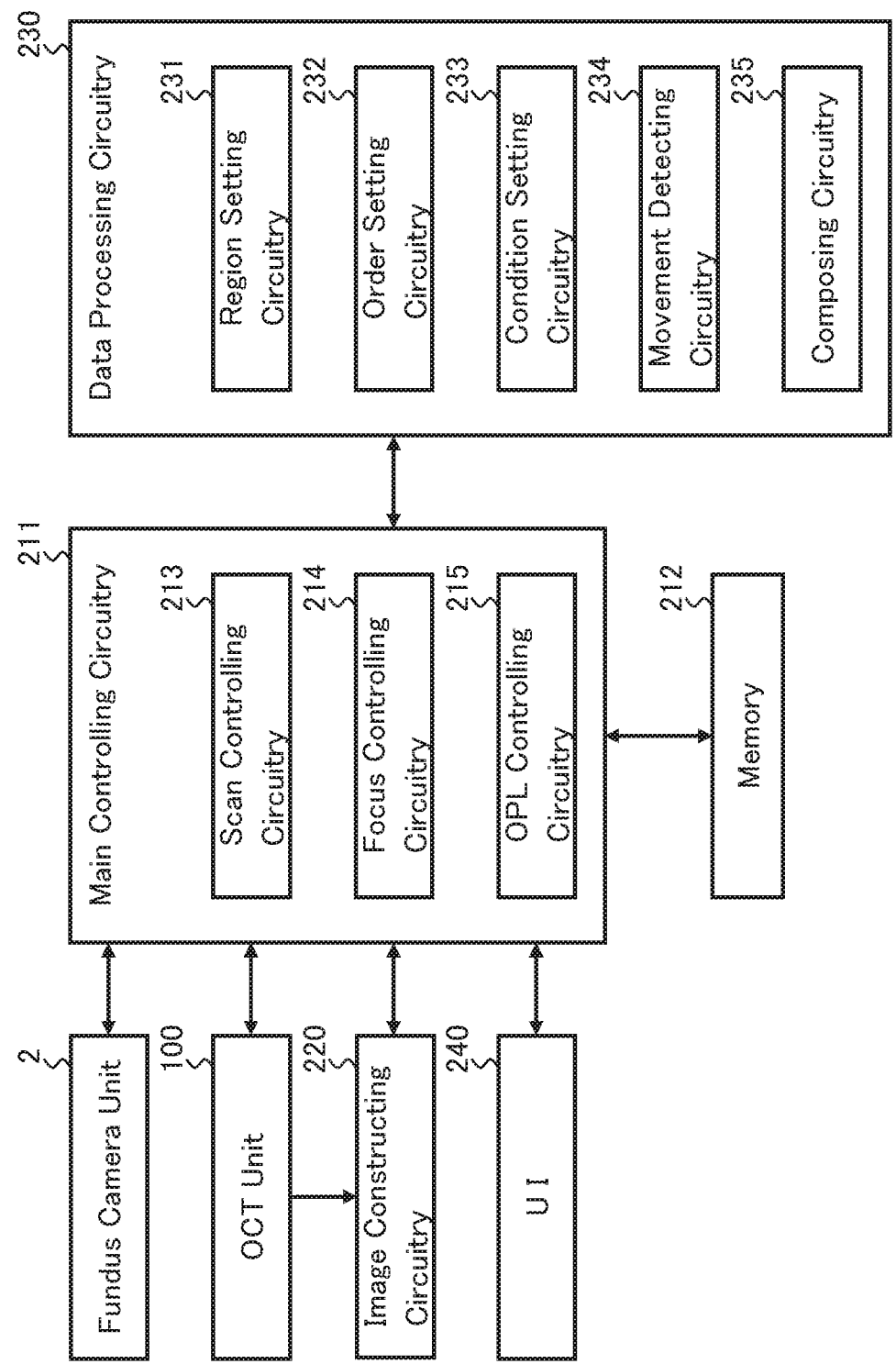
FIG. 4 is a schematic diagram illustrating an example of the configuration of the ophthalmic imaging apparatus according to the exemplary embodiment.

FIG. 3 and FIG. 4 show an example of the configuration of the control system and the processing system of the ophthalmic imaging apparatus 1. The controlling circuitry 210, the image constructing circuitry 220 and the data processing circuitry 230 are provided in the arithmetic control unit 200, for example. The ophthalmic imaging apparatus 1 may include a communication device for performing data communication with an external device. The ophthalmic imaging apparatus 1 may include a drive device (e.g., a reader and/or a writer) for performing a process of reading data from a recording medium and a process of writing data into the recording medium.

<Controlling Circuitry 210>

The controlling circuitry 210 performs various kinds of controls. The controlling circuitry 210 includes the main controlling circuitry 211 and the memory 212. In addition, as shown in FIG. 4, the controlling circuitry 210 of the present embodiment includes the scan controlling circuitry 213, the focus controlling circuitry 214, and the optical path length controlling circuitry (OPL controlling circuitry, for short) 215. They are included in the main controlling circuitry 211.

<Main Controlling Circuitry 211>

The main controlling circuitry 211 includes one or more processors and controls each element of the ophthalmic imaging apparatus 1 (including the elements shown in FIG. 1 to FIG. 4). The main controlling circuitry 211 is realized by the cooperation of hardware including the processors and control software.

The main controlling circuitry 211 can operate any two or all of the scan controlling circuitry 213, the focus controlling circuitry 214, and the OPL controlling circuitry 215 in an interlocking manner (e.g., in a synchronized manner). With this, any two or all of the OCT scanning, the focus adjustment, and the optical path length adjustment are performed in an interlocking manner (e.g., in a synchronized manner).

Under the control of the main controlling circuitry 211, the photography focus driver 31A moves the photography focusing lens 31 disposed in the photographing optical path and the focus optical system 60 disposed in the illumination optical path. Under the control of the main controlling circuitry 211 (specifically, the OPL controlling circuitry 215), the retroreflector driver (RR driver, for short) 41A moves the retroreflector 41 disposed in the measurement arm. Under the control of the main controlling circuitry 211 (specifically, the focus controlling circuitry 214), the OCT focus driver 43A moves the OCT focusing lens 43 disposed in the measurement arm. The optical scanner 44 disposed in the measurement arm operates under the control of the main controlling circuitry 211 (specifically, the scan controlling circuitry 213). The retroreflector driver (RR driver, for short) 114A moves the retroreflector 114 disposed in the reference arm under the control of the main controlling circuitry 211 (specifically, the OPL controlling circuitry 215). Each of the aforesaid drivers includes an actuator, such as a pulse motor, that operates under the control of the main controlling circuitry 211.

The movement mechanism 150 moves, for example, at least the fundus camera unit 2 in a three dimensional manner. In a typical example, the movement mechanism 150 includes the followings: an x stage movable in the ±x direction (i.e., left and right direction); an x movement mechanism that moves the x stage; a y stage movable in the ±y direction (i.e., up and down direction); a y movement mechanism that moves the y stage; a z stage movable in the ±z direction (i.e., depth direction); and a z movement mechanism that moves the z stage. Each of the aforesaid movement mechanisms includes an actuator, such as a pulse motor, that operates under the control of the main controlling circuitry 211.

<Memory 212>

The memory 212 stores various kinds of data. Examples of the data stored in the memory 212 include OCT images, fundus images, subject's eye information, and control parameters.

The subject's eye information includes subject information such as the patient ID and the patient's name, identification information for the left eye and the right eye, and electronic medical record information.

A control parameter includes, for example, a parameter used for control of OCT scanning (referred to as a scan control parameter), a parameter used for focus control such as focal position control or focal distance control (referred to as a focus control parameter), and a parameter used for control of the optical path length of any one or both of the measurement arm and the reference arm (referred to as an optical path length control parameter).

The scan control parameter is a parameter indicating at least the content of control for the optical scanner 44. The scan control parameter may further include a parameter indicating the content of control for the light source unit 101.

Examples of the scan control parameter include a parameter indicating a scan pattern, a parameter indicating a scan rate (or scan speed), and a parameter indicating scan intervals. The scan rate is defined as, for example, an A-scan repetition rate. The scan intervals are defined as, for example, intervals between mutually adjacent A-scans, that is, arrangement intervals of scan points.

The present embodiment performs montage imaging (OCT scanning). The montage imaging applies OCT scans sequentially to a plurality of regions different from each other of the fundus Ef.

Two adjacent regions in montage imaging may be partially in common with each other. In other words, as for the first region and the second region located adjacent to each other among the plurality of regions, part of the first region and part of the second region may overlap each other. This overlapping region (i.e., the common region) is referred to, for example, as a margin for determining the relative position between the first region and the second region in montage (i.e., panorama composition).

The scan control parameters include parameters related to montage imaging carried out in such a way. Exemplary scan control parameters may include a parameter indicating an attribute of the entire region to which montage imaging is applied. Such a parameter is referred to as an entire region parameter.

Other exemplary scan control parameters may include a parameter indicating an attribute of a plurality of regions, each of which is a part of the entire region. Such a parameter is referred to referred to as a partial region parameter.

Still other exemplary scan control parameters may include a parameter indicating an attribute of a plurality of regions different from each other regardless of an entire region determined in advance. The scan control parameters of the present example are also referred to as partial region parameters because the region occupied by the plurality of regions can be considered as an entire region.

The entire region may be a three dimensional region or a two dimensional region when the three dimensional region is viewed from the front. The same applies to partial regions.

An entire region parameter is any parameter relating to the region to which montage imaging is applied. Examples of the entire region parameter include a shape parameter, a size parameter, and a position parameter of the entire region.

An entire region shape parameter is a parameter indicating the shape of the entire region, and is typically a parameter that indicates the shape of the outer edge of the entire region. The outer edge shape of the entire region defined as a two dimensional region may be, for example, a rectangle, a circle, an ellipse, or an arbitrary shape. The outer edge shape of the entire region defined as a three dimensional region may be, for example, a rectangular parallelepiped shape, a spherical shape, an ellipsoidal shape, or an arbitrary shape. The outer edge shape of the entire region may be, for example, any of the followings: the shape of the outer edge of the planar region defined in the xy plane; the shape of the outer edge of the region defined on the fundus surface having a bowl shape (typically a curved surface region); and the shape of the outer edge of the composite image obtained by montage composition.

An entire region size parameter is a parameter that indicates the size (or dimension) of the entire region, and is typically set corresponding to the shape of the entire region. The region size may be typically the size, area, volume or any size information of the outer edge of the entire region. The outer edge size of the entire region defined as a two dimensional region may be, for example, the side length, diameter, radius, major axis, minor axis, or circumferential length. The outer edge size of the entire region defined as a three dimensional region may be, for example, the area of the outer surface, the circumferential length, the maximum circumferential length, or the minimum circumferential length. Further, the size of the entire region may be represented by the angle of view.

An entire region position parameter is a parameter indicating the position of the entire region, and is typically a parameter that indicates the position of a representative point in the entire region. The representative point may be, for example, the center, the center of gravity, the vertex, or another point in the entire region. The position of the representative point may include, for example, information indicating a fixation position, information indicating an OCT scan position, or information indicating a site of the fundus.

The entire region parameter of one specific example indicates that its shape is rectangular, its size is a length of 20 mm in the x direction and a length of 20 mm in the y direction, and, as to its position, the center of the entire region matches the macula (e.g., the fovea centralis). The entire region parameter of another specific example indicates that its shape is substantially circular or substantially elliptic, its size corresponds to the angle of view of 180 degrees, and, as to its position, the center of the entire region corresponds to the fixation position for macular imaging.

The partial region parameter indicates an attribute of a plurality of partial regions to which OCT scans are sequentially applied in montage imaging. The partial region parameter is any parameter relating to the plurality of partial regions. Examples of the partial region parameter include a shape parameter, a size parameter, and a position parameter of each partial region. Such partial region parameters may be defined in the same way as corresponding entire region parameters.

In addition, examples of the partial region parameter include a parameter indicating an arrangement of a plurality of partial regions and a parameter indicating an order of OCT scans applied to a plurality of partial regions.

The focus control parameter is a parameter indicating the content of control for the OCT focus driver 43A. Examples of the focus control parameter include a parameter indicating the focal position of the measurement arm, a parameter indicating the moving speed (velocity) of the focal position, and a parameter indicating the acceleration in the movement of the focal position.

The parameter indicating the focal position is, for example, a parameter indicating the position of the OCT focusing lens 43. The parameter indicating the moving speed of the focal position is, for example, a parameter indicating the moving speed of the OCT focusing lens 43. The parameter indicating the moving acceleration of the focal position is, for example, a parameter indicating the moving acceleration of the OCT focusing lens 43. The moving speed may or may not be constant. The same applies to the moving acceleration.

The focus control parameter may include information corresponding to each of the plurality of partial regions. For example, the focus control parameter may include one or more focal positions corresponding to each partial region.

When two or more focal positions are associated with one partial region, the focus control parameter may include, together with these focal positions, information indicating the area to which each focal position is assigned. The information indicating the areas to which the focal positions are respectively assigned is represented, for example, as information indicating two or more subsets (e.g., two or more identification numbers of B-scan lines) of a whole set that represents a plurality of B-scans included in a concerned partial region.

The optical path length control parameter is a parameter that indicates the content of control for any one or both of the retroreflector driver 41A and the retroreflector driver 114A. Examples of the optical path length control parameter include the followings: a parameter indicating the position of the retroreflector 41; a parameter indicating the moving speed of the retroreflector 41; a parameter indicating the moving acceleration of the retroreflector 41; a parameter indicating the position of the retroreflector 114; a parameter indicating the moving speed of the retroreflector 114; and a parameter indicating the moving acceleration of the retroreflector 114.

The optical path length control parameter may include a plurality of pieces of information respectively corresponding to the plurality of partial regions. For example, the optical path length control parameter may include one or more retroreflector positions corresponding to each partial region.

When two or more retroreflector positions are associated with one partial region, the optical path length control parameter may include, together with these retroreflector positions, information indicating the area to which each retroreflector position is assigned. The information indicating the areas to which the retroreflector positions are respectively assigned is represented, for example, as information indicating two or more subsets (e.g., two or more identification numbers of B-scan lines) of a whole set that represents a plurality of B-scans included in a concerned partial region.

<Scan Controlling Circuitry 213>

The scan controlling circuitry 213 controls the optical scanner 44 based on the scan control parameters. The scan controlling circuitry 213 may further perform control for the light source unit 101. The contents of processing executed by the scan controlling circuitry 213 will be described later. The scan controlling circuitry 213 is realized by the cooperation of hardware including a processor and scan control software.

<Focus Controlling Circuitry 214>

The focus controlling circuitry 214 controls the OCT focus driver 43A based on the focus control parameters. The contents of processing executed by the focus controlling circuitry 214 will be described later. The focus controlling circuitry 214 is realized by the cooperation of hardware including a processor and focus control software.

<Optical Path Length Controlling Circuitry (OPL Controlling Circuitry) 215>

The OPL controlling circuitry 215 controls any one or both of the retroreflector driver 41A and the retroreflector driver 114A based on the optical path length control parameters. The contents of processing executed by the OPL controlling circuitry 215 will be described later. The OPL controlling circuitry 215 is included in the main controlling circuitry 211. The OPL controlling circuitry 215 is realized by the cooperation of hardware including a processor and optical path length control software.

As described above, the present embodiment performs any two or all of the OCT scanning, the focus adjustment, and the optical path length adjustment in an interlocking manner (e.g., in a synchronized manner). Typically, all of the three operations are performed in an interlocking manner. The main controlling circuitry 211 can realize the interlocking operations between the OCT scanning, the focus adjustment, and the optical path length adjustment according to control software for interlockingly operating the scan controlling circuitry 213, the focus controlling circuitry 214, and the OPL controlling circuitry 215.

<Image Constructing Circuitry 220>

The image constructing circuitry 220 includes a processor, and constructs OCT image data of the fundus Ef based on signals (sampling data) input from the data acquisition system 130. The OCT image data is, for example, B-scan image data, that is, two dimensional cross sectional image data.

The processing for constructing OCT image data includes noise elimination (or noise reduction), filtering, fast Fourier transform (FFT), and other processes as in a conventional Fourier domain OCT. In the event where another type of OCT apparatus is used, the image constructing circuitry 220 performs known processing according to the OCT type employed.

The image constructing circuitry 220 constructs three dimensional data of the fundus Ef based on signals input from the data acquisition system 130. The three dimensional data is three dimensional image data representing a three dimensional region (i.e., a volume) of the fundus Ef. Three dimensional image data means image data in which pixel positions are defined using a three dimensional coordinate system. Stack data and volume data are examples of three dimensional image data.

Stack data is image data constructed by three dimensionally arranging a plurality of cross sectional images obtained along a plurality of scan lines, based on the positional relationship of the scan lines. In other words, stack data is image data constructed by representing a plurality of cross sectional images, which are originally defined using individually different two dimensional coordinate systems, using a common single three dimensional coordinate system, that is, by embedding the cross sectional images in a single three dimensional space. Alternatively, stack data is image data constructed by three dimensionally arranging a plurality of pieces of A-scan data obtained respectively for a plurality of scan points arranged in a two dimensional manner (i.e., scan point array), based on the positional relationship of the scan points.

Volume data is image data whose picture elements are voxels that are arranged in a three dimensional manner. Volume data is also referred to as voxel data. Volume data is constructed by applying known interpolation, voxelization, or the like, to stack data.

The image constructing circuitry 220 constructs an image to be displayed, by applying rendering to three dimensional image data. Examples of applicable rendering methods include volume rendering, surface rendering, maximum intensity projection (MIP), minimum intensity projection (MinIP), and multi planar reconstruction (MPR).

The image constructing circuitry 220 may be configured to construct an OCT front image (also referred to as an OCT en-face image) based on three dimensional image data. For example, the image constructing circuitry 220 may be configured to construct projection data by projecting three dimensional image data in the z direction (A-line direction, depth direction). Further, the image constructing circuitry 220 may be configured to construct a shadowgram by projecting partial data of three dimensional image data in the z direction.

Partial three dimensional image data used for the shadowgram construction is set, for example, using segmentation. Segmentation is a process of specifying a partial region in an image. Typically, segmentation is used to specify an image region corresponding to a predetermined tissue of the fundus Ef. Segmentation is performed, for example, by the image constructing circuitry 220 or the data processing circuitry 230.

The ophthalmic imaging apparatus 1 may be capable of performing OCT angiography. OCT angiography is an imaging technique that constructs an image in which retinal blood vessels and choroidal blood vessels are emphasized. This technique is disclosed, for example, in Japanese Unexamined Patent Application Publication (Translation of PCT Application) No. 2015-515894. Generally, fundus tissues (i.e., fundus structures) do not change with time, but the blood flow inside blood vessels change with time. In OCT angiography, an image is generated by emphasizing parts (e.g., blood flow signals) in which such time-dependent changes exist. OCT angiography is also referred to as OCT motion contrast imaging. In addition, images obtained by OCT angiography are referred to as angiographic images, angiograms, motion contrast images, or the like.

When OCT angiography is performed, the ophthalmic imaging apparatus 1 repeatedly scans the same region of the fundus Ef a predetermined number of times. In montage OCT angiography, for example, scans can be applied repeatedly and sequentially to a plurality of partial regions of the arrangement indicated in the scan control parameter, in the order indicated in the scan control parameter. In another example, a series of OCT scans can be repeated a predetermined number of times in the order indicated in the scan control parameter for a plurality of partial regions of the arrangement indicated in the scan control parameter.

The image constructing circuitry 220 can construct a motion contrast image from the data set acquired by the data acquisition system 130 through such repetitive scans. The motion contrast image is an angiographic image imaged by emphasizing a temporal change of the interference signals caused by the blood flow in the fundus Ef. Typically, OCT angiography is applied to a three dimensional region of the fundus Ef, and an image representing a three dimensional distribution of blood vessels of the fundus Ef is obtained.

When OCT angiography is performed, the image constructing circuitry 220 can construct any kind of two dimensional angiographic image data and/or any kind of pseudo three dimensional angiographic image data from three dimensional angiographic image data. For example, the image constructing circuitry 220 can construct two dimensional angiographic image data representing an arbitrary cross section of the fundus Ef by applying multi planar reconstruction to three dimensional angiographic image data. In addition, the image constructing circuitry 220 can construct a front image representing any slab of a shallow layer, middle layer, and deep layer of the retina, or a front image representing a slab of the choroid (such as the choriocapillaris), from three dimensional angiographic image data.

The image constructing circuitry 220 is realized by the cooperation of hardware including a processor and image construction software.

<Data Processing Circuitry 230>

The data processing circuitry 230 includes a processor, and applies various kinds of data processing to an image of the subject's eye E. For example, the data processing circuitry 230 is realized by the cooperation of hardware including a processor and data processing software.

The data processing circuitry 230 can perform position matching (i.e., registration) between two images acquired for the fundus Ef. For example, the data processing circuitry 230 can perform registration between three dimensional image data acquired by OCT and a front image acquired by the fundus camera unit 2. Further, the data processing circuitry 230 can perform registration between two OCT images acquired by OCT. Furthermore, the data processing circuitry 230 can perform registration between two front images acquired by the fundus camera unit 2. In addition, registration can be applied to an analysis result of an OCT image and/or an analysis result of a front image. The registration can be performed by any known method or technique, and includes, for example, feature point extraction and affine transformation.

As illustrated in FIG. 4, the data processing circuitry 230 of the present embodiment includes the region setting circuitry 231, the order setting circuitry 232, the condition setting circuitry 233, the movement detecting circuitry 234, and the composing circuitry 235.

<Region Setting Circuitry 231>

The region setting circuitry 231 sets a plurality of regions (e.g., a plurality of partial regions) to which montage imaging is applied.

The region setting circuitry 231 may be configured to set a plurality of partial regions based on, for example, an OCT image of the fundus Ef of the subject's eye E. Typically, the region setting circuitry 231 performs the following two processes: a process of analyzing an OCT image constructed from data acquired by applying OCT scanning to the fundus Ef, to generate shape information of the fundus Ef; and a process of setting a plurality of partial regions based on the shape information generated.

Figure 5A:
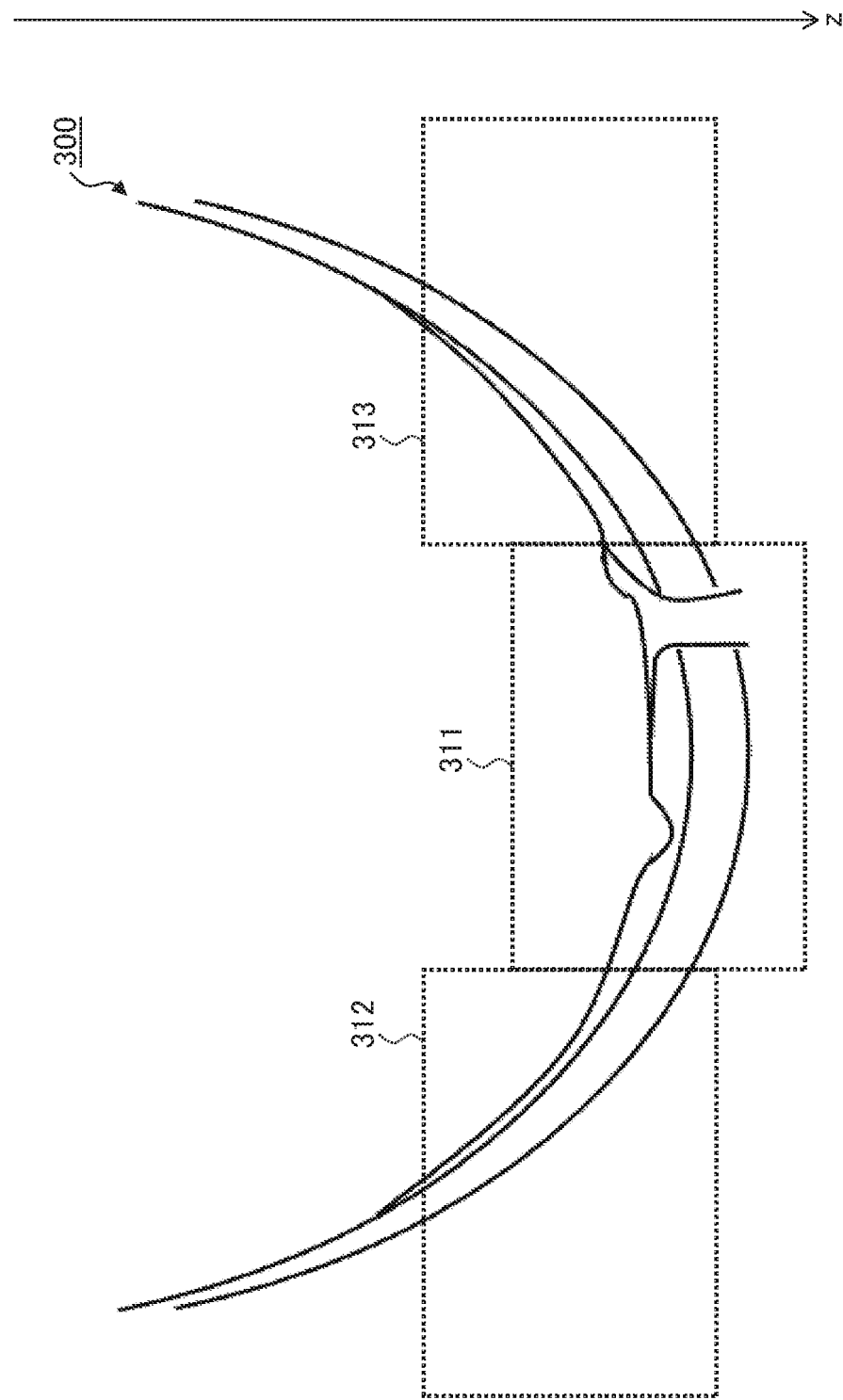
FIG. 5A is a schematic diagram for describing an example of processing performed by the ophthalmic imaging apparatus according to the exemplary embodiment.

An example of processing executable by the region setting circuitry 231 will be described with referring to FIG. 5A and FIG. 5B. The reference symbol 300 of FIG. 5A shows an OCT image (B-scan image) of the fundus Ef. The B-scan image 300 is constructed from the data acquired by the B-scan 320 shown in FIG. 5B.

As can be seen from the B-scan image 300, the fundus shape (e.g., the fundus surface shape, the retina surface shape, the inner limiting membrane shape) is generally a bowl-like shape having a deep central part and a shallow peripheral part. Furthermore, there are individual differences in fundus shapes. For example, in the case of high myopia, the difference in depth between the central part and the peripheral part tends to be large, and the fundus shape tends to be distorted due to posterior staphyloma.

The region setting circuitry 231 analyzes the B-scan image 300 to obtain shape information indicating the shape of the fundus Ef. Exemplary shape information includes a depth position distribution indicating depth positions (z coordinates) at a plurality of positions on the fundus Ef.

For example, the region setting circuitry 231 may be configured to apply segmentation to the B-scan image 300 to specify an image region corresponding to a predetermined site of the fundus Ef (e.g., fundus surface, nerve fiber layer, ganglion cell layer, retinal pigment epithelium layer, etc.), and then create a depth position distribution (e.g., a distribution of z coordinates) of the specified image region.

In addition, the region setting circuitry 231 can set a plurality of partial regions based on the depth position distribution. For example, the region setting circuitry 231 may be configured to specify the depth position corresponding to each of the plurality of partial regions from the depth position distribution, and then determine the z position of the each partial region based on the depth positions specified.

Figure 5B:
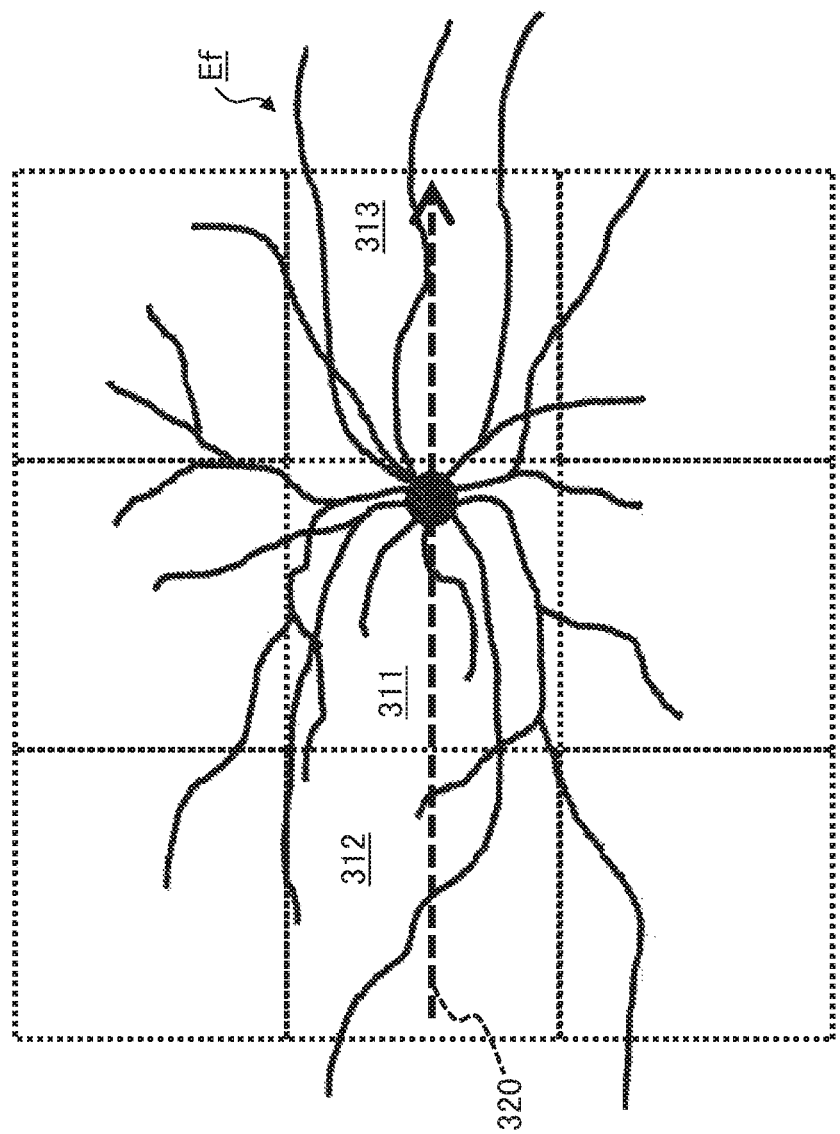
FIG. 5B is a schematic diagram for describing an example of processing performed by the ophthalmic imaging apparatus according to the exemplary embodiment.

In the present example, as shown in FIG. 5B, the nine partial regions arranged in 3 rows×3 columns are set. Each of these partial regions is square-shaped in the xy plane. Any pair of partial regions adjacent to one another share the boundary with each other (that is, the above-mentioned margin is not provided). In the present example, the entire region is also square-shaped in the xy plane.

On the other hand, in the z direction, the partial region 311 that is set at the central part of the fundus Ef is arranged on the +z side compared to the partial regions 312 and 313 that are set at the peripheral parts, as shown in FIG. 5A. Thus, the positions (typically z positions) of the plurality of partial regions are set in accordance with the shape (typically the depth position distribution) of the fundus Ef.

In the example shown in FIG. 5A and FIG. 5B, the shapes and sizes of all the plurality of partial regions in the xy plane are the same. However, the aspects of partial regions are not limited to this. An example in which the shapes and sizes are different will be described with referring to FIG. 6A and FIG. 6B.

Figure 6A:
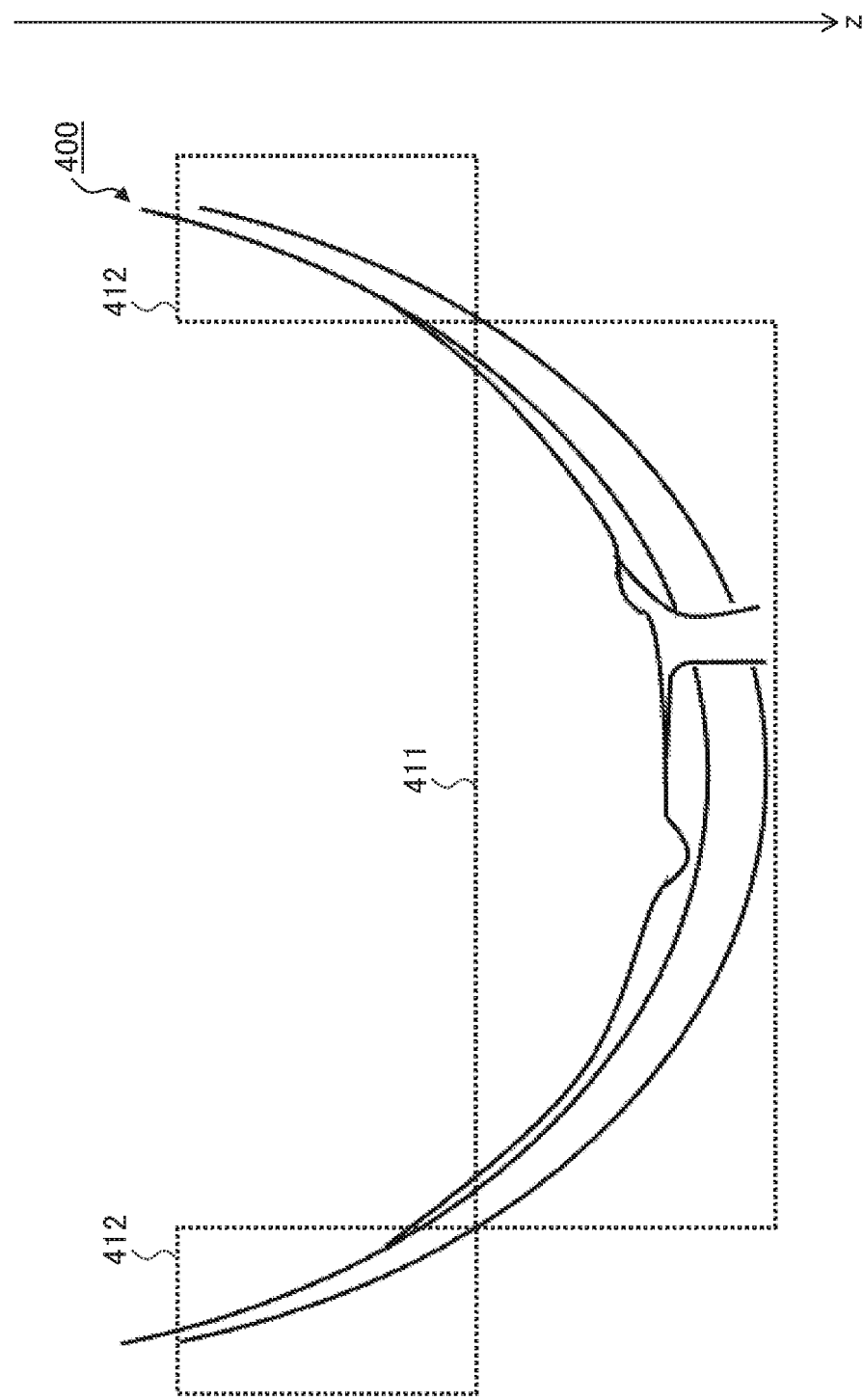
FIG. 6A is a schematic diagram for describing an example of processing performed by the ophthalmic imaging apparatus according to the exemplary embodiment.

The reference symbol 400 in FIG. 6A shows an OCT image (B-scan image) of the fundus Ef. The B-scan image 400 is constructed from data acquired by the B-scan 420 shown in FIG. 6B.

The region setting circuitry 231 analyzes the B-scan image 400 to obtain shape information indicating the shape of the fundus Ef. Exemplary shape information includes a depth position distribution. The region setting circuitry 231 can set a plurality of partial regions based on the depth position distribution. For example, the region setting circuitry 231 can specify the depth position corresponding to each of the plurality of partial regions from the depth position distribution, and determine the z position of each partial region based on the depth positions specified.

Figure 6B:
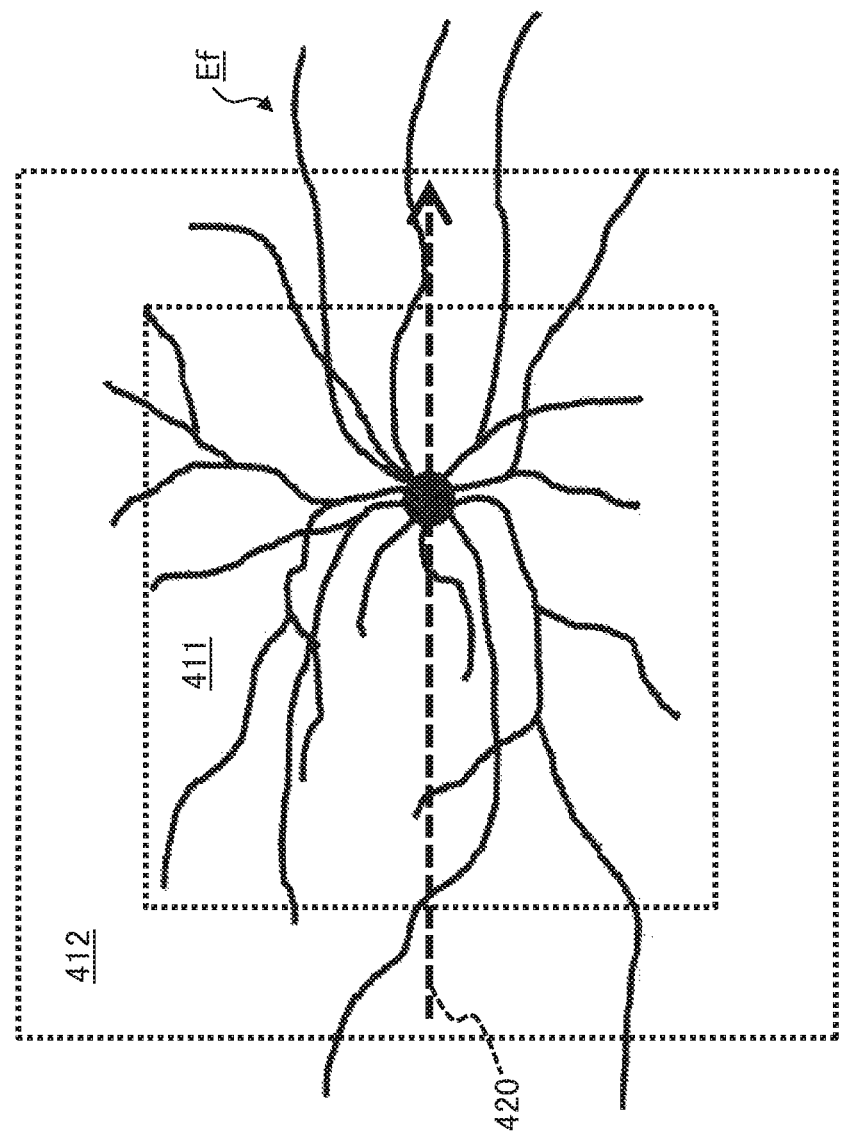
FIG. 6B is a schematic diagram for describing an example of processing performed by the ophthalmic imaging apparatus according to the exemplary embodiment.

In the present example, as shown in FIG. 6B, the partial region (the central partial region) 411 arranged in the central part of the fundus Ef is set, and the partial region (the peripheral partial region) 412 arranged in the periphery of the fundus (in the peripheral part of the fundus) is set. The central partial region 411 is square-shaped in the xy plane. The peripheral partial region 412 is a shape defined by two concentric squares in the xy plane. The outer edge of the central partial region 411 and the inner edge of the peripheral partial region 412 are common (that is, the above-described margin is not provided). The entire region of the present example is square-shaped in the xy plane.

On the other hand, in the z direction, the central partial region 411 is arranged on the +z side relative to the peripheral partial region 412, as shown in FIG. 6A. Thus, the positions (typically z positions) of the plurality of partial regions are set in accordance with the shape (typically the depth position distribution) of the fundus Ef.

In some examples described above, a B-scan is applied to the fundus Ef to grasp an approximate shape of the fundus Ef, and a plurality of partial regions are set from the approximate shape. The OCT scan mode (e.g., scan pattern) for grasping tan approximate shape of the fundus Ef is not limited to B-scans, but may be any OCT scan mode that can be used to recognize the fundus shape (typically, the depth position distribution). Examples of such OCT scan modes are a radial scan, a cross scan, a multiline scan, a multicross scan, a raster scan, and a spiral scan.

Some examples described above set a plurality of partial regions for montage imaging, based on an OCT image obtained by actually applying an OCT scan to the fundus Ef of the subject's eye E; however, the region setting circuitry 231 may be configured to set a plurality of partial regions for montage imaging based on a standard fundus shape.

In this case, standard shape information indicating a standard fundus shape obtained from clinical data, a schematic eye (model eye), and/or an eye model is generated and stored in the memory 212. The region setting circuitry 231 can perform the setting of a plurality of partial regions based on the standard shape information in the same manner as in the case based on an actual OCT image of the fundus Ef. Typically, the standard shape information includes a depth position distribution of a standard fundus, and the region setting circuitry 231 can set a plurality of partial regions based on the depth position distribution.

Two or more pieces of standard shape information can be prepared and used in a selective manner. For example, standard shape information corresponding to normal eyes (e.g., healthy eyes, healthy-seeming eyes) and standard shape information corresponding to high myopia can be prepared. In addition, considering the fact that high myopia eyes exhibit various eye ball shapes (e.g., various posterior pole shapes), it is possible to prepare a plurality of pieces of standard shape information according to a known ocular posterior pole shape classification.

When two or more pieces of standard shape information are prepared, the ophthalmic imaging apparatus 1 receives information indicating the fundus shape of the subject's eye E. For example, the ophthalmic imaging apparatus 1 can receive fundus shape information of the subject's eye E from a server, a computer, or a recording medium using the communication device or drive device described above. The fundus shape information is typically included in medical data such as an electronic medical record, an interpretation report, or a summary.

Alternatively, the ophthalmic imaging apparatus 1 can display a screen presenting a plurality of options of the fundus shape, on the display device 241. In this case, the user can use the operation device 242 to select one of the options corresponding to the eye morphology of the subject's eye E.

The region setting circuitry 231 can set a plurality of partial regions for montage imaging based on the standard shape information selected from the two or more pieces of standard shape information.

The region setting circuitry 231 is realized by the cooperation of hardware including a processor and region setting software.

<Order Setting Circuitry 232>

The order setting circuitry 232 sets the order in which the OCT scans are applied to the partial regions for montage imaging in accordance with the fundus shape of the subject's eye E.

For example, the order setting circuitry 232 may be configured to set a plurality of partial regions based on an OCT image of the fundus Ef of the subject's eye E. Typically, the order setting circuitry 232 performs the following two processes: a process of analyzing an OCT image constructed from data acquired by applying an OCT scan to the fundus Ef, to generate shape information of the fundus Ef; and a process of setting the order of the OCT scans applied to the partial regions based on the shape information generated.

Typically, the order setting circuitry 232 is configured to obtain a depth position distribution of the fundus Ef as shape information, and set an OCT scan application order based on the depth position distribution.

The generation of the shape information can be performed in the same manner as that of the region setting circuitry 231. When the region setting circuitry 231 has already generated the shape information, the order setting circuitry 232 can use the shape information generated by the region setting circuitry 231. Conversely, when the order setting circuitry 232 has already generated the shape information, the region setting circuitry 231 can use the shape information generated by the order setting circuitry 232.

Figure 7:
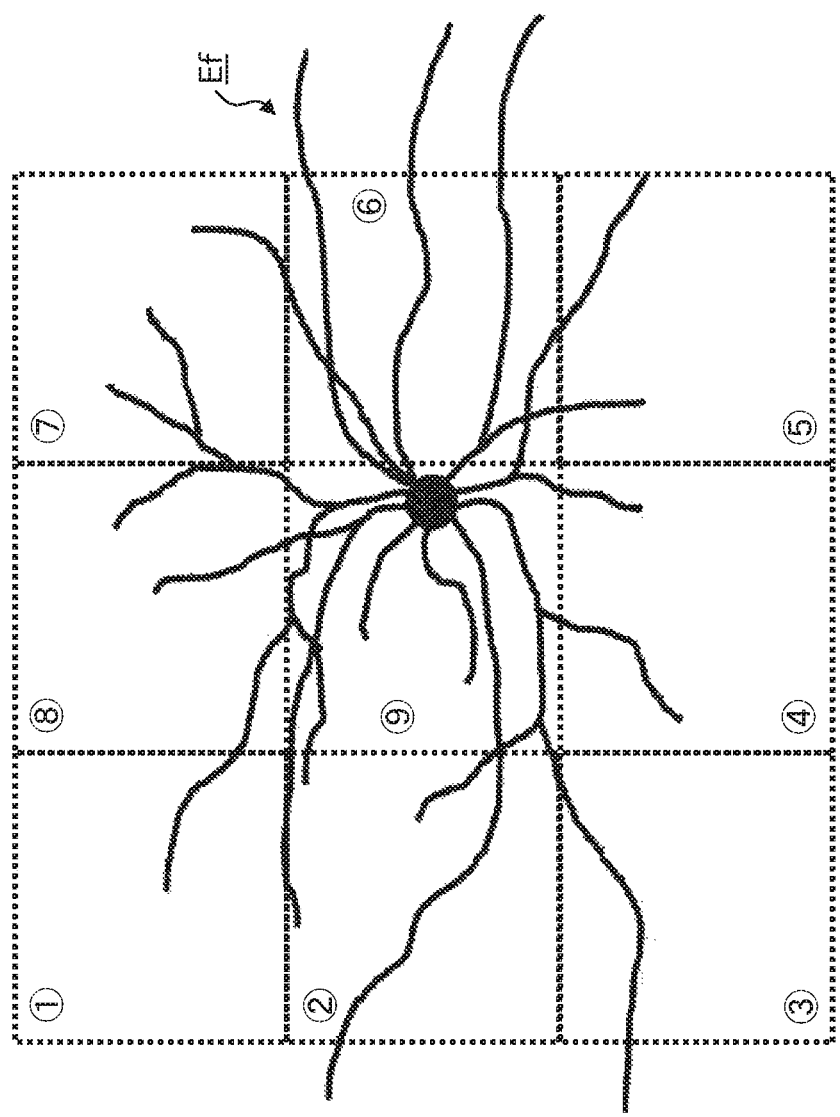
FIG. 7 is a schematic diagram for describing an example of processing performed by the ophthalmic imaging apparatus according to the exemplary embodiment.

As one specific example, when the region setting circuitry 231 sets the nine partial regions shown in FIG. 5A and FIG. 5B, the order setting circuitry 232 sets the order shown in FIG. 7 for the nine partial regions based on the shape information generated by the region setting circuitry 231, for example. More specifically, the order setting circuitry 232 assigns the order of the first to eighth to eight partial regions among the nine partial regions arranged in 3 rows×3 columns. Here, the eight partial regions are those arranged around the central partial region, and the order is assigned sequentially from the upper left partial region to the upper middle partial region in a counterclockwise manner. Further, the order setting circuitry 232 assigns the order of the ninth to the central partial region.

This ordering is made according to the fundus shape. In the present example, the order setting circuitry 232 first classifies the nine partial regions into one central partial region and eight peripheral partial regions based on their depth position distributions. Here, the central partial region is arranged at the deepest location (utmost+z side) and the peripheral partial regions are the rest. Further, the order setting circuitry 232 assigns the order of the ninth to the central partial region, and assigns the order of the first to eighth to the eight peripheral partial regions.

Here, the order setting circuitry 232 may assign the order of the first to the central partial region while assigning the order of the second to ninth to the eight peripheral partial regions.

In addition, the order for the eight partial regions is not limited to the example shown in FIG. 7. For example, the order setting circuitry 232 may be configured to assign the order to the eight partial regions according to a predetermined direction. Alternatively, the order setting circuitry 232 may be configured to acquire the depth position (e.g., z coordinate) of each of the partial regions, and assign the order to the partial regions in descending or ascending order of the z coordinates acquired.

As another specific example, when the region setting circuitry 231 sets the two partial regions shown in FIG. 6A and FIG. 6B, the order setting circuitry 232 can assign order to the two partial regions in an arbitrarily way.

Some examples described above set the application order of OCT scans to partial regions for montage imaging, based on an OCT image obtained by actually applying an OCT scan to the fundus Ef of the subject's eye E; however, the order setting circuitry 232 may be configured to set the application order of OCT scans on the basis of a standard fundus shape. In this case, standard shape information like that used in the case of setting partial regions can be used. Further, two or more pieces of standard shape information can be prepared and used in a selective manner.

The order setting circuitry 232 is realized by the cooperation of hardware including a processor and order setting software.

<Condition Setting Circuitry 233>

The condition setting circuitry 233 sets conditions for applying OCT scans to partial regions for montage imaging in accordance with the fundus shape of the subject's eye E. The conditions set by the condition setting circuitry 233 may include any of the control parameters described above (e.g., the scan control parameters, the focus control parameters, and the optical path length control parameters).

For example, for each of the partial regions for montage imaging, the condition setting circuitry 233 may be configured to: analyze an OCT image acquired by applying a preparatory OCT scan to a concerned partial region, to determine a depth position of the fundus Ef in the concerned partial region; and set a condition applied to the concerned partial region for montage imaging.

Instead of applying the preparatory OCT scans individually to the plurality of partial regions as described above, the condition setting circuitry 233 may be configured to: apply a preparatory OCT scan to obtain an approximate shape of the region of the fundus Ef corresponding to the entire of the plurality of partial regions (the entire region); and set conditions for the plurality of partial regions from an image obtained by the preparatory OCT scan.

The condition setting circuitry 233 may be configured to obtain a depth position distribution of the fundus Ef as the shape information, and set the conditions respectively applied to the OCT scans for the plurality of partial regions based on the depth position distribution.

The generation of the shape information can be performed in the same manner as that of the region setting circuitry 231 or of the order setting circuitry 232. When the region setting circuitry 231 or the order setting circuitry 232 has already generated shape information, the condition setting circuitry 233 can use this shape information generated by the region setting circuitry 231 or the order setting circuitry 232. Conversely, when the condition setting circuitry 233 has already generated shape information, the region setting circuitry 231 or the order setting circuitry 232 can use this shape information generated by the condition setting circuitry 233.

As one specific example, when setting the optical path length control parameters based on the depth position distribution, the condition setting circuitry 233 may determine, for each of the plurality of partial regions, the depth position of a concerned partial region from the depth position distributions, and determine any one or both of the position of the retroreflector 41 and the position of the retroreflector 114 corresponding to the depth position determined. The retroreflector positions thus obtained respectively for the plurality of partial regions are applied at the times of performing OCT scans on corresponding partial regions in montage imaging. That is, when performing an OCT scan on a concerned partial region of the plurality of partial regions in the montage imaging, the OPL controlling circuitry 215 controls any one or both of the retroreflector driver 41A and the retroreflector driver 114A in such a way that the retroreflector position determined for the concerned partial region is realized.

As another specific example, when setting the focus control parameters based on the depth position distribution, the condition setting circuitry 233 may determine, for each of the plurality of partial regions, the depth position of a concerned partial region from the depth position distribution, and determine the position of the OCT focusing lens 43 corresponding to the depth position determined for the concerned partial region. The position of the OCT focusing lens 43 thus obtained is applied at the time of performing an OCT scan on its corresponding partial region in montage imaging. That is, when applying an OCT scan to a partial region in the montage imaging, the focus controlling circuitry 214 controls the OCT focus driver 43A so that the OCT focusing lens 43 is disposed at the position determined for this partial region.

The condition setting circuitry 233 is realized by the cooperation of hardware including a processor and condition setting software.

<Movement Detecting Circuitry 234>

The ophthalmic imaging apparatus 1 includes the fundus camera unit 2 that repeatedly photographs the subject's eye E to acquire a time-series image. The time-series image acquired by the fundus camera unit 2 is an observation image mentioned above, for example.

The movement detecting circuitry 234 analyzes the observation image acquired by the fundus camera unit 2 to detect the movement of the subject's eye E. For example, the movement detecting circuitry 234 analyzes each image (i.e., each frame) included in the observation image to detect a feature point, and obtains a temporal change in the feature point position. The feature point may be the center, the center of gravity, of the contour of the pupil, or may be the center, the center of gravity, or the contour of the iris, for example.

The scan controlling circuitry 213 can control the optical scanner 44 based on the output from the movement detecting circuitry 234 while controlling the optical scanner 44 and the OCT unit 100 according to the scan control parameters. The control of the optical scanner 44 on the basis of the output from the movement detecting circuitry 234 is so-called tracking control.

Tracking is executed by the series of processing, described below, disclosed in, for example, Japanese Unexamined Patent Application Publication No. 2017-153543. To begin with, the movement detecting circuitry 234 registers, as a reference image, a frame (i.e., a front image) of the observation image acquired by the fundus camera unit 2.

Further, the movement detecting circuitry 234 determines the change in the position of the feature point in another frame relative to the position of the feature point in the reference image. This process corresponds to determining the temporal change in the position of the feature point, that is, determining the positional differences between the reference image and other frames. In the case where the positional difference exceeds a threshold value or the positional difference cannot be detected due to blinking or fixation error, the movement detecting circuitry 234 can register a frame acquired thereafter as a new reference image. Further, the method or technique of obtaining the temporal change in the feature point position is not limited to this. For example, the deviation (displacement) of the feature point between two consecutive frames may be sequentially obtained.

The movement detecting circuitry 234 sends control information for canceling (that is, for eliminating) the temporal change to the scan controlling circuitry 213 each time the temporal change in the feature point position is calculated. The scan controlling circuitry 213 corrects the orientation of the optical scanner 44 based on the control information input in a sequential manner.

The movement detecting circuitry 234 is realized by the cooperation of hardware including a processor and movement detecting software.

<Composing Circuitry 235>

The composing circuitry 235 constructs a composite image of a plurality of OCT images constructed by montage imaging. Image composition is performed by a known method or technique.

When mutually adjacent two OCT images have a margin, the compositing circuitry 235 can determine the relative position between the two OCT images in such a way that the position of the image depicted in the margin in one of the two OCT images matches the position of the image depicted in the margin in the other.

When no margin is given, the composing circuitry 235 can determine the arrangement of the plurality of OCT images corresponding to the plurality of partial regions according to the arrangement of the plurality of partial regions set by the region setting circuitry 231, for example.

<User Interface 240>

The user interface 240 includes the display device 241 and the operation device 242. The display device 241 includes the display device 3. The operation device 242 includes various kinds of operation devices and input devices. The user interface 240 may include, for example, a device such as a touch panel in which a display function and an operation function are integrated. It is also possible to construct an embodiment that does not include at least part of the user interface 240. For example, the display device may be an external device connected to the ophthalmic imaging apparatus.

<Operation>

The operation of the ophthalmic imaging apparatus 1 will be described. Note that it is assumed that preparatory operations same as or similar to conventional preparatory operations have already been performed prior to the exemplary operation described below. The preparatory operations include, for example, input of a patient ID, presentation of a fixation target, adjustment of a fixation position, alignment, focus adjustment, OCT optical path length adjustment, and the like.

An example of the operation of the ophthalmic imaging apparatus 1 will be described with referring to FIG. 8.

(S1: Apply Preparatory OCT Scan to Fundus to Acquire Preparatory Image)

First, the ophthalmic imaging apparatus 1 applies a preparatory OCT scan to the fundus Ef using the optical scanner 44, the OCT unit 100, etc. The image constructing circuitry 220 constructs a preparatory image from data acquired by the preparatory OCT scan. The preparatory image is sent to each of the region setting circuitry 231, the order setting circuitry 232, and the condition setting circuitry 233.

(S2: Set Partial Regions, Scan Order, and Scan Conditions)

The region setting circuitry 231 sets a plurality of partial regions for montage imaging based on the preparatory image obtained in step S1. In the present example, it is assumed that the nine partial regions shown in FIG. 5A and FIG. 5B are set. Information indicating the determined partial regions is stored in the memory 212.

The order setting circuitry 232 sets the order of OCT scans to be performed on the partial regions set by the region setting circuitry 231, based on the preparatory image obtained in step S1. In the present example, it is assumed that the scan order shown in FIG. 7 is assigned to the nine partial regions shown in FIG. 5A and FIG. 5B. Information indicating the determined scan order is stored in the memory 212.

The condition setting circuitry 233 sets conditions to be applied in the OCT scans for the partial regions set by the region setting circuitry 231, based on the preparatory image obtained in step S1. In the present example, it is assumed that at least an optical path length control parameter and a focus control parameter are set for each of the nine partial regions shown in FIG. 5A and FIG. 5B. The scan conditions determined are stored in the memory 212.

(S3: Start Montage Imaging)

After the end of step S2, the ophthalmic imaging apparatus 1 starts montage imaging. The ophthalmic imaging apparatus 1 starts montage imaging in response to a predetermined imaging trigger. The imaging trigger is, for example, a signal indicating the end of step S2 or a signal indicating a user's instruction.

Upon receiving the imaging trigger, the main controlling circuitry 211 performs control for the optical scanner 44 or the LCD 39 (the fixation position) in order to apply an OCT scan to the first partial region (that is, upper left partial region) of the nine partial regions set in step S2. This process is carried out by the scan controlling circuitry 213.

(S4: Perform Control for Scan Conditions)

The OPL controlling circuitry 215 controls any one or both of the retroreflector driver 41A and the retroreflector driver 114A based on the optical path length control parameters set in step S2, to set the optical path length of the interference optical system to an optical path length according to the depth position of a concerned partial region.

Further, the focus controlling circuitry 214 controls the OCT focus driver 43A based on the focus control parameters set in step S2, to set the focus state (e.g., focal position or focal length) of the measurement arm of the interference optical system to an focus state according to the depth position of the concerned partial region.

In addition to these, the ophthalmic imaging apparatus 1 may perform adjustment of the polarization controller 118, adjustment of the polarization controller 103, adjustment of the attenuator 120, etc. The adjustment of the polarization controller 118 is performed for optimizing the interference efficiency and the interference intensity between the measurement light LS and the reference light LR. Typically, the adjustment of the polarization controller 118 is performed by feedback control of the polarization controller 118 using results of monitoring interference signals. The same applies to the adjustment of the polarization controller 103 and the adjustment of the attenuator 120.

(S5: Apply OCT Scan to Partial Region)

The scan controlling circuitry 213 applies an OCT scan to the concerned partial region based on the scan control parameters set in step S2.

(S6: Have All Partial Regions Been Scanned?)

After the OCT scans have already been applied to all of the nine partial regions set in step S2 (S6: Yes), the process proceeds to step S8.

On the other hand, when the OCT scan has not been applied to any of the nine partial regions set in step S2 (S6: No), the process proceeds to step S7.

(S7: Proceed to Next Partial Region)

When it is determined in step S6 that there is a partial region to which an OCT scan has not been applied yet (S6: No), the scan controlling circuitry 213 specifies the partial region to which an OCT scan is applied next based on the scan order set in step S2. Furthermore, the scan controlling circuitry 213 performs control for the optical scanner 44 or the LCD 39 (i.e., the fixation position) in order to apply the OCT scan to the next partial region specified. Then, the process returns to step S4.

By repeatedly executing steps S4 to S7 until it is determined "Yes" in step S6, the ophthalmic imaging apparatus 1 can apply the OCT scans to all the partial regions set in step S2, under the scan conditions (e.g., the optical path lengths, focus states, polarization states, etc.) according to the respective depth positions of the partial regions, and in the order according to the depth positions of the partial regions.

(S8: Construct Images of Partial Regions)

After the OCT scans have been applied to all of the plurality of partial regions set in step S2 (S6: Yes), the process proceeds to step S8.

In step S8, for each of the plurality of partial regions set in step S2, the image constructing circuitry 220 constructs an OCT image from the data acquired by the OCT scan to the concerned partial region. In the present example, typically, raster scan is applied to each partial region, and a three dimensional image corresponding to each partial region is constructed. Thereby, a plurality of three dimensional images respectively corresponding to the plurality of partial regions are obtained.

(S9: Construct Composite Image)

The composing circuitry 235 constructs a composite image corresponding to a region (referred to as an entire region) formed by the union of the plurality of partial regions, by composing the plurality of three dimensional images corresponding to the plurality of partial regions constructed in step S8 (End).

The data processing circuitry 230 can perform rendering on the composite image constructed by the composing circuitry 235. The main controlling circuitry 211 can display an image constructed by the rendering on the display device 241.

Figure 8:
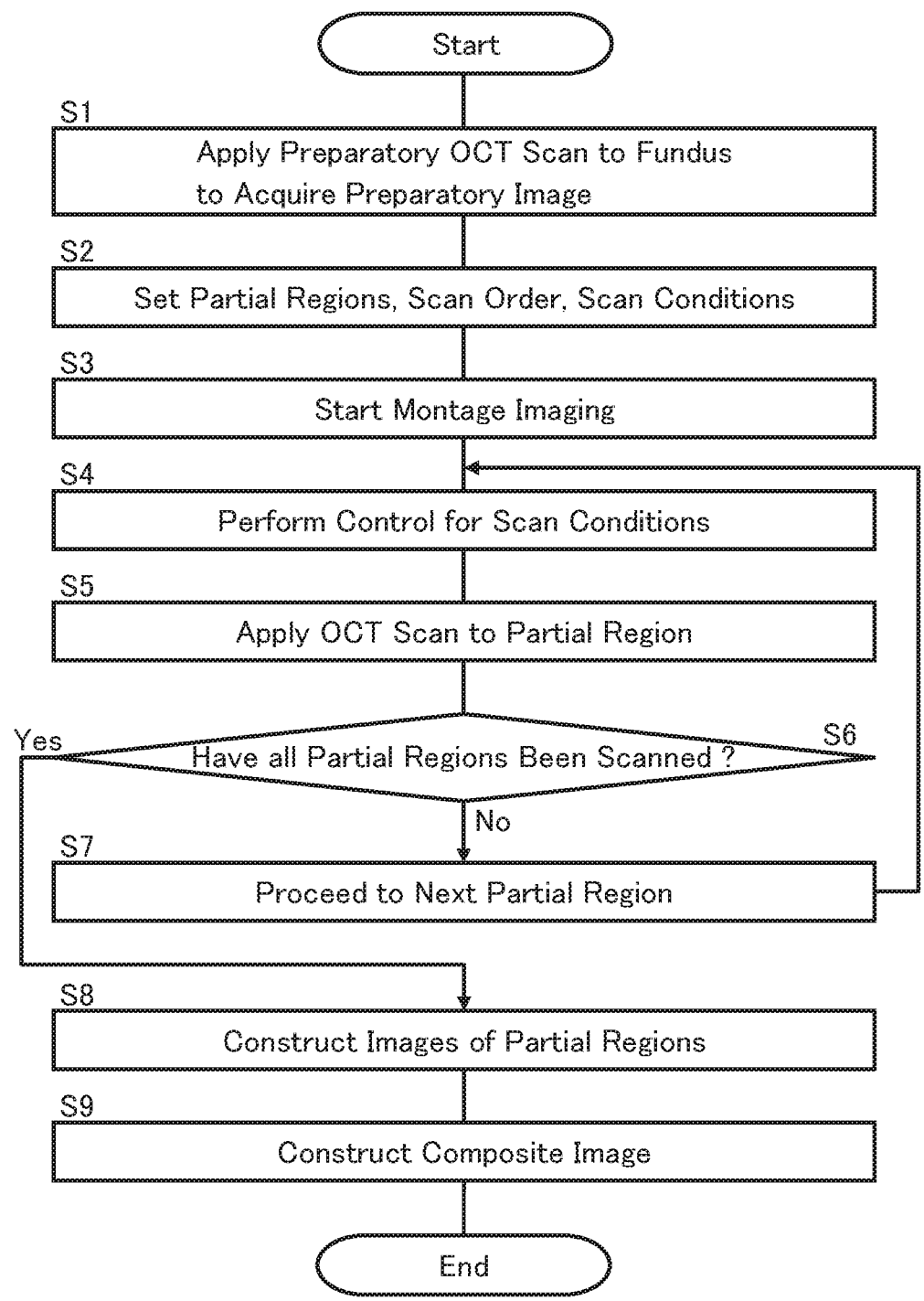
FIG. 8 is a flowchart showing an example of the operation of the ophthalmic imaging apparatus according to the exemplary embodiment.

In the operation example shown in FIG. 8, the ophthalmic imaging apparatus 1 performs, prior to montage imaging, a series of processes including the preparatory OCT scan, preparatory image construction, generation of shape information of the fundus Ef, and setting of scan conditions of the plurality of partial regions for montage imaging.

On the other hand, the ophthalmic imaging apparatus 1 may be configured to perform this series of processes during montage imaging. For example, the ophthalmic imaging apparatus 1 may be configured to perform, for each of the partial regions, the series of processes including a preparatory OCT scan, preparatory image construction, generation of shape information of the fundus Ef, and setting of scan conditions of a concerned partial region. In the present example, each time a partial region is switched to a new partial region, the ophthalmic imaging apparatus 1 performs a preparatory OCT scan on the new partial region, constructs a preparatory image of the new partial region, generates shape information of the region of the fundus Ef corresponding to the new partial region, and sets scan conditions for the new partial region. Then, the ophthalmic imaging apparatus 1 applies an OCT scan for montage imaging to the new partial region. After the completion of the OCT scan, the operation shifts to the same processes for the next partial region. Such a series of processes is sequentially performed on the plurality of partial regions in the order according to the fundus shape.

<Actions and Effects>

Some actions and effects of some exemplary embodiments will be described.

The ophthalmic imaging apparatus (1) according to some exemplary embodiments includes a data acquisition device, image constructing circuitry, and composing circuitry.

The data acquisition device is configured to sequentially apply OCT scans to a plurality of regions different from each other of the fundus (Ef) of the subject's eye (E) in order and under a condition both according to a fundus shape, thereby acquiring a plurality of pieces of data corresponding to the plurality of regions.

In the above example, the data acquisition device includes the OCT unit 100 and the elements in the fundus camera unit 2 that constitutes the measurement arm (the retroreflector 41, the OCT focusing lens 43, the optical scanner 44, the objective lens 22, etc.).

The data acquisition device of the above example is configured to sequentially apply OCT scans to a plurality of partial regions different from each other of the eye fundus (Ef) in order and under conditions both according to a fundus shape of the subject's eye (E) or a standard fundus shape (e.g., optical path length, focus state, polarization state), thereby acquiring a plurality of pieces of data corresponding to the plurality of partial regions. Here, the process of switching the target of an OCT scan from one partial region to the next partial region is performed by any one or both of control of the optical scanner 44 and control of the LCD 39 (i.e., the fixation target).

The image constructing circuitry is configured to construct an image from each of the plurality of pieces of data acquired by the data acquisition device corresponding to the plurality of regions. In the above example, the image constructing circuitry includes the image constructing circuitry 220.

The composing circuitry is configured to construct a composite image of the plurality of images constructed from the plurality of pieces of data by the image constructing circuitry. In the above example, the composing circuitry includes the composing circuitry 235.

According to some exemplary embodiments thus configured, the ophthalmic imaging apparatus can apply the OCT scans to the plurality of regions of the eye fundus in the order and under the conditions both according to the fundus shape. By setting both the scan order and the scan conditions according to the fundus shape in this way, the switching of the scan conditions accompanying the switching of the regions to which the OCT scans are applied can be performed without prolonging the time taken for the montage imaging.

For example, with conventional techniques, changing the conditions carried out by moving an optical element using an actuator (e.g., focus adjustment, optical path length adjustment, etc.) takes time as compared to the operation of an optical scanner. Therefore, switching of the regions cannot be performed at high speed.

In contrast, in some exemplary embodiments, for example, the ophthalmic imaging apparatus can change the scan areas from a deep part towards a shallow part of the eye fundus while gradually changing the optical path length, the focal position, etc. from a deep side towards a shallow side of the eye fundus.

As a result, the amount of change in the scan conditions (e.g., the change amount in the optical path length, the movement amount of the focal position, etc.) accompanying the switching of the scan areas becomes smaller. This shortens the time taken to change the scan conditions as compared to those of conventional cases, and further leads to shortening the time taken for montage imaging in comparison to conventional cases. In other words, the ophthalmic imaging apparatus of some exemplary embodiments can shorten the time required for montage imaging while appropriately changing the scan conditions for improving the image quality at high speed. Therefore, some exemplary embodiments contribute to both the shortening of time required for montage imaging and the improvement of the image quality.

The ophthalmic imaging apparatus according to some exemplary embodiments further includes order setting circuitry configured to set a scan order according to the fundus shape. In the above example, the order setting circuitry includes the order setting circuitry 232.

By providing the order setting circuitry thus configured, the setting of scan order can be performed using the ophthalmic imaging apparatus itself. With this, the setting of scan order and the montage imaging according to the scan order can be performed by using the ophthalmic imaging apparatus according to the exemplary embodiments alone.

In some exemplary embodiments, the data acquisition device may be configured to apply a preparatory OCT scan to the eye fundus prior to applying the OCT scans to the plurality of regions of the fundus. (i.e., prior to montage imaging) Further, the image constructing circuitry may be configured to construct a preparatory image from the data acquired through the preparatory OCT scan. In addition, the order setting circuitry may be configured to analyze the preparatory image to generate shape information on the fundus of the subject's eye and set the scan order based on the shape information generated.

According to such exemplary embodiments, the measurement of the fundus shape of the subject's eye, the setting of the scan order based on the measurement result of the fundus shape, and the montage imaging according to the scan order can be performed by using the ophthalmic imaging apparatus according to the exemplary embodiments alone.

In some exemplary embodiments, the order setting circuitry may be configured to determine a depth position distribution of the fundus of the subject's eye as the shape information, and set the scan order based on the depth position distribution determined.

According to such exemplary embodiments, the depth position distribution of the fundus of the subject's eye can be used to set an appropriate scan order of the plurality of regions in an order according to the depth positions.

In some exemplary embodiments, the order setting circuitry may be configured to set the scan order based on standard shape information indicating a standard fundus shape generated in advance.

According to such exemplary embodiments, scan conditions can be set using the standard fundus shape when the fundus shape of the subject's eye cannot be measured or when a measurement result of fundus shape cannot be obtained.

The ophthalmic imaging apparatus according to some exemplary embodiments may further include region setting circuitry that sets a plurality of regions to which montage imaging is applied. In the above example, the region setting circuitry includes the region setting circuitry 231.

By providing the region setting circuitry thus configured, the setting of the plurality of regions subjected to the montage imaging can be performed using the ophthalmic imaging apparatus itself.

In some exemplary embodiments, the data acquisition device may be configured to apply a preparatory OCT scan to the fundus of the subject's eye prior to applying the OCT scans to the plurality of regions (i.e., prior to montage imaging). Furthermore, the image constructing circuitry may be configured to construct a preparatory image from the data acquired through the preparatory OCT scan. In addition, the region setting circuitry is configured to analyze the preparatory image to generate shape information on the fundus of the subject's eye and set the plurality of regions for montage imaging based on the shape information generated.

According to such exemplary embodiments, the measurement of the fundus shape of the subject's eye, the setting of the plurality of regions based on the measurement result of the fundus shape, and the montage imaging for the plurality of regions can be performed by using the ophthalmic imaging apparatus according to the exemplary embodiments alone.

In some exemplary embodiments, the region setting circuitry may be configured to set the plurality of regions for montage imaging based on standard shape information indicating a standard fundus shape generated in advance.

According to such exemplary embodiments, the plurality of regions for montage imaging can be set using the standard fundus shape when the fundus shape of the subject's eye cannot be measured or when the measurement result of the fundus shape cannot be obtained.

The ophthalmic imaging apparatus according to some exemplary embodiments may include condition setting circuitry configured to set the scan conditions according to the fundus shape. In the above example, the condition setting circuitry includes the condition setting circuitry 233.

By providing the condition setting circuitry thus configured, the setting of the scan conditions can be performed using the ophthalmic imaging apparatus itself.

In some exemplary embodiments, the data acquisition device may be configured to apply a preparatory OCT scan to each of the plurality of regions for montage imaging. Further, the image constructing circuitry may be configured to construct a preparatory image of each region from data acquired from that region through the preparatory OCT scan. In addition, the condition setting circuitry may be configured to analyze the preparatory image of each region to determine a depth position of the fundus in that region and set a scan condition applied to an OCT scan of that region based on the depth position determined for that region.

Alternatively, in some exemplary embodiments, the data acquisition device may be configured to apply a preparatory OCT scan to the fundus of the subject's eye prior to applying the OCT scans to the plurality of regions for montage imaging. Further, the image constructing circuitry may be configured to construct a preparatory image from data acquired through the preparatory OCT scan. In addition, the condition setting circuitry may be configured to analyze the preparatory image to generate shape information on the fundus of the subject's eye and set scan conditions respectively applied to the OCT scans for the plurality of regions based on the shape information.

According to such exemplary embodiments, the measurement of the fundus shape of the subject's eye, the setting of the scan conditions based on the measurement result of the fundus shape, and the montage imaging based on the scan conditions can be performed by using the ophthalmic imaging apparatus according to the exemplary embodiments alone.

In some exemplary embodiments, the condition setting circuitry may be configured to determine a depth position distribution of the fundus of the subject's eye as the shape information and set the scan conditions respectively applied to the OCT scans for the plurality of regions based on the depth position distribution.

According to such exemplary embodiments, it becomes possible to set appropriate scan conditions such as appropriate optical path lengths and appropriate focal positions using the depth position distribution of the fundus of the subject's eye.

In some exemplary embodiments, the condition setting circuitry may be configured to set the scan conditions respectively applied to the OCT scans for the plurality of regions for montage imaging based on standard shape information indicating a standard fundus shape generated in advance.

According to such exemplary embodiments, the scan conditions for montage imaging can be set using the standard fundus shape when the fundus shape of the subject's eye cannot be measured or when the measurement result of the fundus shape cannot be obtained.

In some exemplary embodiments, the data acquisition device may include a measurement arm that forms a path of measurement light projected onto the fundus of the subject's eye for the OCT scans and a reference arm that forms a path of reference light superposed on the measurement light. Further, the scan conditions may include an arm length condition that indicates at least one of the length of the measurement arm and the length of the reference arm.

In addition, the ophthalmic imaging apparatus according to some exemplary embodiments may include an arm length changing device and the first controlling circuitry.

The arm length changing device is configured to change at least one of the length of the measurement arm and the length of the reference arm. In the above example, the arm length changing device includes any one or both of the combination of the retroreflector 41 and the retroreflector driver 41A, and the combination of the retroreflector 114 and the retroreflector driver 114A.

The first controlling circuit is configured to control the arm length changing device based on the arm length conditions. In the above example, the first controlling circuitry includes the optical path length controlling circuitry 215.

According to such exemplary embodiments, it is possible to perform OCT optical path length adjustment according to the fundus shape in the montage imaging carried out in the order according to the fundus shape. This leads to the improvement of the image quality.

In some exemplary embodiments, the scan conditions include a focus condition that indicates a focus state (e.g., focal position, focal length) of the measurement arm that forms the path of the measurement light projected onto the fundus of the subject's eye for the OCT scans.

In addition, the ophthalmic imaging apparatus according to some exemplary embodiments may include a focus state changing device and the second controlling circuitry.

The focus state changing device is configured to change the focus state of the measurement arm. In the above example, the focus state changing device includes the OCT focusing lens 43 and the OCT focus driver 43A.

The second controlling circuitry is configured to control the focus state changing device based on the focus conditions. In the above example, the second controlling circuitry includes the focus controlling circuitry 214.

According to such exemplary embodiments, it is possible to perform OCT focus adjustment according to the fundus shape in the montage imaging carried out in the order according to the fundus shape. This leads to the improvement of the image quality.

Some exemplary embodiments provide a method and technique of controlling an ophthalmic imaging apparatus. The ophthalmic imaging apparatus to which this control method is applied includes a data acquisition device configured to acquire data by applying an OCT scan to the fundus of the subject's eye, and a processor configured to process data acquired by the data acquisition device. In the above example, the data acquisition device includes the OCT unit 100 and the elements in the fundus camera unit 2 that constitutes the measurement arm (the retroreflector 41, the OCT focusing lens 43, the optical scanner 44, the objective lens 22, etc.). Further, in the above example, the processor includes the image constructing circuitry 220 and the data processing circuitry 230 (at least the composing circuitry 235).

The control method includes a data acquisition step, an image construction step, and a composition step. The data acquisition step sequentially applies OCT scans to a plurality of regions different from each other of the fundus of the subject's eye in order and under a condition both according to a fundus shape, to acquire a plurality of pieces of data corresponding to the plurality of regions. The image construction step constructs an image from each of the plurality of pieces of data. The composition step constructs a composite image of the plurality of images constructed from the plurality of pieces of data by the image construction step.

It is possible to combine any of the items (configurations, elements, operations, etc.) described in the exemplary embodiments with the control method of the ophthalmic imaging apparatus.

Some exemplary embodiments provide a program that causes a computer to execute such a control method of the ophthalmic imaging apparatus. The program can be combined with any of the items described in the exemplary embodiments.

Further, it is possible to create a computer-readable non-transitory recording medium storing such a program. It is possible to combine any of the items described in the exemplary embodiments with the recording medium. The non-transitory recording medium may have any form, and examples thereof include a magnetic disk, an optical disk, a magneto-optical disk, a semiconductor memory, and the like.

According to the method, the program, or the recording medium according to some exemplary embodiments, it is possible to achieve both shortening of time required for montage imaging and improvement of image quality. In addition, actions and effects are exhibited according to items combined with the method, the program, or the recording medium according to the exemplary embodiments.

While certain embodiments have been described, these embodiments have been presented by way of example only, and are not intended to limit the scope of the inventions. Indeed, the novel embodiments described herein may be embodied in a variety of other forms; furthermore, various omissions, substitutions, additions and changes in the form of the embodiments described herein may be made without departing from the spirit of the inventions. The accompanying claims and their equivalents are intended to cover such forms or modifications as would fall within the scope and spirit of the inventions.

EXPLANATION OF SYMBOLS 1 ophthalmic imaging apparatus
41 retroreflector
41A retroreflector driver (RR driver)
43 OCT focusing lens
43A OCT focus driver
100 OCT unit
114 retroreflector
114A retroreflector driver (RR driver)
118 polarization controller
210 controlling circuitry
211 main controlling circuitry
212 memory
213 scan controlling circuitry
214 focus controlling circuitry
215 optical path length controlling circuitry (OPL controlling circuitry)
220 image constructing circuitry
230 data processing circuitry
231 region setting circuitry
232 order setting circuitry
233 condition setting circuitry
235 composing circuitry

What is claimed is:

1. An ophthalmic imaging apparatus comprising:
   a data acquisition device that sequentially applies optical coherence tomography (OCT) scans to a plurality of regions different from each other of a fundus of a subject's eye in order and under a condition according to a fundus shape, to acquire a plurality of pieces of data corresponding to the plurality of regions;
   image constructing circuitry that constructs an image from each of the plurality of pieces of data;
   composing circuitry that constructs a composite image of a plurality of images constructed from the plurality of pieces of data by the image constructing circuitry; and
   order setting circuitry that sets the order according to the fundus shape, wherein
   the data acquisition device applies a preparatory OCT scan to the fundus prior to applying the OCT scans to the plurality of regions,
   the image constructing circuitry constructs a preparatory image from data acquired through the preparatory OCT scan, and
   the order setting circuitry analyzes the preparatory image to generate shape information on the fundus and sets the order based on the shape information.

2. The ophthalmic imaging apparatus of claim 1, wherein the order setting circuitry determines a depth position distribution of the fundus as the shape information and sets the order based on the depth position distribution.

3. An ophthalmic imaging apparatus comprising:
   a data acquisition device that sequentially applies optical coherence tomography (OCT) scans to a plurality of regions different from each other of a fundus of a subject's eye in order and under a condition according to a fundus shape, to acquire a plurality of pieces of data corresponding to the plurality of regions;
   image constructing circuitry that constructs an image from each of the plurality of pieces of data;

composing circuitry that constructs a composite image of a plurality of images constructed from the plurality of pieces of data by the image constructing circuitry; and region setting circuitry that sets the plurality of regions, wherein the data acquisition device applies a preparatory OCT scan to the fundus prior to applying the OCT scans to the plurality of regions, the image constructing circuitry constructs a preparatory image from data acquired through the preparatory OCT scan, and the region setting circuitry analyzes the preparatory image to generate shape information on the fundus and sets the plurality of regions based on the shape information.

4. An ophthalmic imaging apparatus comprising:

a data acquisition device that sequentially applies optical coherence tomography (OCT) scans to a plurality of regions different from each other of a fundus of a subject's eye in order and under a condition according to a fundus shape, to acquire a plurality of pieces of data corresponding to the plurality of regions;

image constructing circuitry that constructs an image from each of the plurality of pieces of data;

composing circuitry that constructs a composite image of a plurality of images constructed from the plurality of pieces of data by the image constructing circuitry; and region setting circuitry that sets the plurality of regions, wherein the region setting circuitry sets the plurality of regions based on standard shape information indicating a standard fundus shape generated in advance.

5. An ophthalmic imaging apparatus comprising:

a data acquisition device that sequentially applies optical coherence tomography (OCT) scans to a plurality of regions different from each other of a fundus of a subject's eye in order and under a condition according to a fundus shape, to acquire a plurality of pieces of data corresponding to the plurality of regions;

image constructing circuitry that constructs an image from each of the plurality of pieces of data;

composing circuitry that constructs a composite image of a plurality of images constructed from the plurality of pieces of data by the image constructing circuitry; and condition setting circuitry that sets the condition according to the fundus shape, wherein the data acquisition device applies a preparatory OCT scan to the fundus, the image constructing circuitry constructs a preparatory image from data acquired from the region through the preparatory OCT scan, and the condition setting circuitry analyzes the preparatory image to set the condition.

6. The ophthalmic imaging apparatus of claim 5, wherein for each of the plurality of regions, the data acquisition device applies a preparatory OCT scan to a region, the image constructing circuitry constructs a preparatory image of the region from data acquired from the region through the preparatory OCT scan, and the condition setting circuitry analyzes the preparatory image of the region to determine a depth position of the fundus in the region and sets a condition applied to an OCT scan of the region based on the depth position.

7. The ophthalmic imaging apparatus of claim 5, wherein the data acquisition device applies the preparatory OCT scan to the fundus prior to applying the OCT scans to the plurality of regions, the image constructing circuitry constructs the preparatory image from data acquired through the preparatory OCT scan, and the condition setting circuitry analyzes the preparatory image to generate shape information on the fundus and sets conditions respectively applied to the OCT scans for the plurality of regions based on the shape information.

8. The ophthalmic imaging apparatus of claim 7, wherein the condition setting circuitry determines a depth position distribution of the fundus as the shape information and sets the conditions respectively applied to the OCT scans for the plurality of regions based on the depth position distribution.

9. An ophthalmic imaging apparatus comprising:

a data acquisition device that sequentially applies optical coherence tomography (OCT) scans to a plurality of regions different from each other of a fundus of a subject's eye in order and under a condition according to a fundus shape, to acquire a plurality of pieces of data corresponding to the plurality of regions;

image constructing circuitry that constructs an image from each of the plurality of pieces of data; and composing circuitry that constructs a composite image of a plurality of images constructed from the plurality of pieces of data by the image constructing circuitry, wherein the data acquisition device includes a measurement arm that forms a path of measurement light projected onto the fundus for the OCT scans and a reference arm that forms a path of reference light superposed on the measurement light, and the condition includes at least one of an arm length condition and a focus condition, the arm length condition indicating at least one of a length of the measurement arm and a length of the reference arm, and the focus condition indicating a focus state of the measurement arm, and the ophthalmic imaging apparatus further comprises controlling circuitry that performs control based at least on the arm length condition and the focus condition.

10. The ophthalmic imaging apparatus of claim 9, further comprising:

an arm length changing device that changes at least one of the length of the measurement arm and the length of the reference arm, wherein the controlling circuitry includes first controlling circuitry that controls the arm length changing device based on the arm length condition.

11. The ophthalmic imaging apparatus of claim 9, further comprising:

a focus state changing device that changes the focus state of the measurement arm, wherein the controlling circuitry includes second controlling circuitry that controls the focus state changing device based on the focus condition.

* * * * *